(12) United States Patent
Livingston et al.

(10) Patent No.: US 12,338,450 B2
(45) Date of Patent: Jun. 24, 2025

(54) GENE THERAPY CONSTRUCTS FOR TREATING WILSON DISEASE

(71) Applicant: Ultragenyx Pharmaceutical Inc., Novato, CA (US)

(72) Inventors: Christine Livingston, Lambertville, NJ (US); Samuel Wadsworth, Shrewsbury, MA (US)

(73) Assignee: Ultragenyx Pharmaceutical Inc., Novato, CA (US)

( * ) Notice: Subject to any disclaimer, the term of this patent is extended or adjusted under 35 U.S.C. 154(b) by 933 days.

(21) Appl. No.: 17/417,619

(22) PCT Filed: Jan. 3, 2020

(86) PCT No.: PCT/US2020/012131
§ 371 (c)(1),
(2) Date: Jun. 23, 2021

(87) PCT Pub. No.: WO2020/142653
PCT Pub. Date: Jul. 9, 2020

(65) Prior Publication Data
US 2022/0090131 A1 Mar. 24, 2022

Related U.S. Application Data

(60) Provisional application No. 62/834,830, filed on Apr. 16, 2019, provisional application No. 62/788,324, filed on Jan. 4, 2019.

(51) Int. Cl.
*C12N 15/86* (2006.01)
*A61K 48/00* (2006.01)
*A61P 43/00* (2006.01)

(52) U.S. Cl.
CPC .......... *C12N 15/86* (2013.01); *A61K 48/0058* (2013.01); *A61P 43/00* (2018.01)

(58) Field of Classification Search
None
See application file for complete search history.

(56) References Cited

U.S. PATENT DOCUMENTS

| | | |
|---|---|---|
| 8,999,380 B2 | 4/2015 | Bancel et al. |
| 11,147,887 B2 | 10/2021 | Murillo Sauca et al. |
| 11,473,106 B2 | 10/2022 | Wilson et al. |
| 2003/0228282 A1 | 12/2003 | Gao et al. |
| 2006/0136184 A1 | 6/2006 | Gustafsson et al. |
| 2014/0032186 A1 | 1/2014 | Gustafsson et al. |
| 2014/0196176 A1* | 7/2014 | Heintz ............... C12N 15/1003 536/25.4 |
| 2015/0111955 A1* | 4/2015 | High ...................... C12N 15/86 435/456 |
| 2015/0315612 A1 | 11/2015 | Wilson et al. |
| 2017/0348435 A1 | 12/2017 | Murillo Sauca et al. |
| 2019/0338310 A1 | 11/2019 | Wilson et al. |

FOREIGN PATENT DOCUMENTS

| | | | |
|---|---|---|---|
| DE | 10156121 A1 | 5/2003 | |
| WO | WO-2003/052051 A2 | 6/2003 | |
| WO | WO-2011/126808 A2 | 10/2011 | |
| WO | WO-2013/049493 A1 | 4/2013 | |
| WO | WO-2015/012924 A2 | 1/2015 | |
| WO | WO-2016/097218 A1 | 6/2016 | |
| WO | WO-2016097219 A1 * | 6/2016 | ............. A61K 38/46 |
| WO | WO-2016/181123 A1 | 11/2016 | |
| WO | WO-2017/100676 A1 | 6/2017 | |
| WO | WO-2018/126116 A1 | 7/2018 | |
| WO | WO-2020/102723 A1 | 5/2020 | |
| WO | WO-2020/142653 A1 | 7/2020 | |

OTHER PUBLICATIONS

Shanmugavel et al. Metallomics, 2017, 9, 981-988 (Year: 2017).*
Hasan et al. J Biol Chem. Aug. 16, 2012;287(43):36041-36050 (Year: 2012).*
Leng et al. Long-Term Correction of Copper Metabolism in Wilson's Disease Mice with AAV8 Vector Delivering Truncated ATP7B; Human Gene Therapy 30 (12), 2019, 1494-1504 (Year: 2019).*
Grote et al, JCat: a novel tool to adapt codon usage of a target gene to its potential expression host, Nucleic Acids Research 33:W526-W531; doi:10.1093/nar/gki376, 2005 (Year: 2005).*
Daniel et al, ATGme: Open-source web application for rare codon identification and custom DNA sequence optimization, BMC Bioinformatics 16: 303, 6 pages, doi. 10.1186/s12859-015-0743-5; 2015 (Year: 2015).*
Fumoto et al, Targeted Gene Delivery: Importance of Administration Routes, INTECH, Novel Gene Therapy Approaches, p. 3-31; editors Wei and Good, publisher Books on Demand, 2013 (Year: 2013).*
Daya et al, Gene Therapy Using Adeno-Associated Virus Vectors, Clin. Microbiol. Rev. 21(4): 583-593, 2008 (Year: 2008).*
Tian et al, Aerosol Inhalation-mediated Delivery of an Adeno-associated Virus 5-expressed Antagonistic Interleukin-4 Mutant Ameliorates Experimental Murine Asthma, Archives of Medical Research 50: 384-392, 2019 (Year: 2019).*
Mingozzi and High, Immune responses to AAV vectors: overcoming barriers to successful gene therapy, Blood 122(1): 23-36, 2013 (Year: 2013).*
Kattenhorn et al, Adeno-Associated Virus Gene Therapy for Liver Disease, Human Gene Therapy 27(12): 947-961, Nov. 28, 2016 (Year: 2016).*

(Continued)

*Primary Examiner* — Maria G Leavitt
*Assistant Examiner* — Alexandra F Connors
(74) *Attorney, Agent, or Firm* — Goodwin Procter LLP

(57) ABSTRACT

This application relates to adeno-associated viral vectors encoding a truncated yet functional ATP7B for use in gene therapy for treating Wilson disease (WD). The truncated ATP7B described herein has several advantages over the wild-type ATP7B such as higher efficacy and improved manufacturing yield.

18 Claims, 11 Drawing Sheets
Specification includes a Sequence Listing.

(56) References Cited

OTHER PUBLICATIONS

Perrin, Make mouse studies work, Nature (507): 423-425, 2014 (Year: 2014).*
Greenberg, Gene Therapy for heart failure, Trends in Cardiovascular Medicine 27: 216-222, 2017 (Year: 2017).*
Maguire et al, Viral vectors for gene delivery to the inner ear, Hearing Research 394: e107927, 13 pages, doi.org/10.1016/j.heares.2020.107927, 2020 (Year: 2020).*
Tobias, Mouse Study Used in Research, Multiple Sclerosis News Today, multiplesclerosisnewstoday.com/news-posts/2023/09/08/lets-not-get-overexcited-about-any-mice-study-used-research/; Sep. 8, 2023; (Year: 2023).*
Bartee et al., "The loop connecting metal-binding domains 3 and 4 of ATP7B is a target of a kinase-mediated phosphorylation," Biochemistry, 2009, 48(24): 5573-5581.
Bernard et al., "Hepatic lesions in 90 captive nondomestic felids presented for autopsy," Vet Pathol. 2015, 52(2): 369-376.
Braiterman et al., "Communication between the N and C termini is required for copper-stimulated Ser/Thr phosphorylation of Cu(I)-ATPase (ATP7B)," Journal of Biological Chemistry, 2015, 290(14): 8803-8819.
Buiakova et al., "Null mutation of the murine ATP7B (Wilson disease) gene results in intracellular copper accumulation and late-onset hepatic nodular transformation," Hum Mol Genet., 1999, 8(9),1665-71.
Calcedo et al., "Worldwide epidemiology of neutralizing antibodies to adeno-associated viruses," J Infect Dis., 2009, 199(3), 381-90.
Cardone et al., "Correction of Hunter syndrome in the MPSII mouse model by AAV2/8-mediated gene delivery", Hum Mol Genet. 2006, 15(7): 1225-1236.
Coronado et al., "The Jackson toxic milk mouse as a model for copper loading," Mamm Genome, 2001, 12(10), 793-795.
Davidoff et al., "Sex significantly influences transduction of murine liver by recombinant adeno-associated viral vectors through an androgen-dependent pathway," Blood, 2003, 102(2), 480-488.
European Association for the Study of the Liver, EASL Clinical Practice Guidelines: Wilson's disease, J Hepatol. 2012, 56(3):671-85.
Gao et al., "Adeno-associated viruses undergo substantial evolution in primates during natural infections," Proc Natl Acad Sci USA, 2003, 13, 100(10), 6081-6.
Gao et al., "Biology of AAV serotype vectors in liver-directed gene transfer to nonhuman primates," Mol Ther., 2006, 13(1), 77-87.
Gourdon et al., "Structural models of the human copper P-type ATPases ATP7A and ATP7B," Biol Chem. 2012, 393(4), 205-16.
Gray et al., "Urinary copper elevation in a mouse model of Wilson's disease is a regulated process to specifically decrease the hepatic copper load," PLoS One, 2012, 7(6):e38327 (10 pages).
Greig et al., "A Gene Therapy Approach to Improve Copper Metabolism and Prevent Liver Damage in a Mouse Model of Wilson Disease," Human Gene Therapy Clin Dev. 2019, 30(1): 29-39.
Greig et al., "Characterization of adeno-associated viral vector-mediated human Factor VIII gene therapy in hemophilia A Mice," Human Gene Therapy 2017, 28(5), 392-402.
Grimm et al., "Titration of AAV-2 particles via a novel capsid ELISA: packaging of genomes can limit production of recombinant AAV-2," Gene Ther., 1999, 6(7), 1322-30.
Hasan et al., "Molecular events initiating exit of a copper-transporting ATPase ATP7B from the trans-golgi network," Journal of Biological Chemistry, 2012, 287(43):36041-36050.
Huster et al., "Consequences of copper accumulation in the livers of the Atp7b$^{-/-}$ (Wilson disease gene) knockout mice," Am J Pathol., 2006, 168(2), 423-34.
Huster et al., "The distinct roles of the N-terminal copper-binding sites in regulation of catalytic activity of the Wilson's disease protein," J Biol Chem., 2003, 278(34), 32212-8.
International Search Report and Written Opinion for corresponding International Application No. PCT/US2020/012131, dated Mar. 30, 2020.
Irani et al., "Correction of liver disease following transplantation of normal rat hepatocytes into Long-Evans cinnamon rats modeling Wilson's disease," Mol Ther., 2001, 3(3), 302-9.
Lock et al., "Absolute determination of single-stranded and self-complementary adeno-associated viral vector genome titers by droplet digital PCR," Hum Gene Ther Methods, 2014, 25(2), 115-25.
Lock et al., "Rapid, simple, and versatile manufacturing of recombinant adeno-associated viral vectors at scale," Hum Gene Ther., 2010, 21(10), 1259-71.
Lutsenko et al., "Function and regulation of human copper-transporting ATPases," Physiol Rev., 2007, 87(3), 1011-46.
McIntosh et al., "Therapeutic levels of FVIII following a single peripheral vein administration of rAAV vector encoding a novel human factor VIII variant," Blood, 2013, 121(17), 3335-44.
McMillin et al., "Direct measurement of free copper in serum or plasma ultrafiltrate," Am J Clin Pathol., 2009, 131(2), 160-5.
Michalczyk et al., "ATP7B expression in human breast epithelial cells is mediated by lactational hormones," J Histochem Cytochem., 2008, 56(4), 389-99.
Miyatake et al., "Transcriptional targeting of herpes simplex virus for cell-specific replication," J Virol., 1997, 71(7), 5124-32.
Murillo et al., "Long-term metabolic correction of Wilson's disease in a murine model by gene therapy," J Hepatol, 2016, 64(2), 419-426.
Petrukhin et al., "Mapping, cloning and genetic characterization of the region containing the Wilson disease gene," Nat Genet. 1993, 5(4), 338-43.
Roberts EA and Schilsky ML, American Association for Study of Liver D. Diagnosis and treatment of Wilson disease: an update, Hepatology., 2008, 47(6), 2089-111.
Roybal et al., "Early gestational gene transfer with targeted ATP7B expression in the liver improves phenotype in a murine model of Wilson's disease," Gene Ther., 2012, 19(11), 1085-94.
Safaei et al., "The role of metal binding and phosphorylation domains in the regulation of cisplatin-induced trafficking of ATP7B," Metallomics, 2013, 5(8), 964-72 (17 pages).
Sandig et al., "HBV-derived promoters direct liver-specific expression of an adenovirally transduced LDL receptor gene," Gene Ther., 1996, 3(11), 1002-9.
Sasaki et al., "The gene responsible for LEC hepatitis, located on rat chromosome 16, is the homolog to the human Wilson disease gene," Biochem Biophys Res Commun., 1994, 202(1), 512-8.
Schosinsky et al., "Measurement of Ceruloplasmin From its Oxidase Activity in Serum by Use of O-dianisidine Dihydrochloride," Clin Chem, 1974, 20(12), 1556-63.
Shanmugavel et al., "Copper relay path through the N-terminus of Wilson disease protein, ATP7B," Metallomics, 2019, 11(9): 1472-1480.
Shanmugavel et al., "Probing functional roles of Wilson disease protein (ATP7B) Copper-binding domains in yeast," Metallomics, 2017, 9(7), 981-988.
Smedley et al., "Copper-associated hepatitis in Labrador retrievers," Vet Pathol. 2009, 46(3), 484-90.
Sommer et al., "Quantification of adeno-associated virus particles and empty capsids by optical density measurement," Mol Ther., 2003, 7(1), 122-8.
Stromeyer FW and Ishak KG, Histology of the liver in Wilson's disease: a study of 34 cases, Am J Clin Pathol., 1980, 73(1), 12-24.
Tanzi et al., "The Wilson disease gene is a copper transporting ATPase with homology to the Menkes disease gene," Nat Genet. 1993, 5(4), 344-50.
Terada K and Sugiyama T, The Long-Evans Cinnamon rat: an animal model for Wilson's disease, Pediatr Int., 1999, 41(4), 414-8.
Theophilos et al., "The toxic milk mouse is a murine model of Wilson disease," Hum Mol Genet, 1996, 5(10), 1619-1624.
Thompson et al., "A comprehensive comparison of multiple sequence alignments," Nucleic Acids Res., 1999, 27(13), 2682-90.
Thornburg et al., "Hereditary copper toxicosis in West Highland white terriers," Vet Pathol., 1986, 23(2), 148-54.
Toole et al., "A large region (approximately equal to 95 kDa) of human factor VIII is dispensable for in vitro procoagulant activity," Proc Natl Acad Sci USA, 1986, 83(16), 5939-42.

(56) References Cited

OTHER PUBLICATIONS

Ward et al., "Codon optimization of human factor VIII cDNAs leads to high-level expression," Blood, 2011, 117(3), 798-807.
Wobus et al., "Monoclonal antibodies against the adeno-associated virus type 2 (AAV-2) capsid: epitope mapping and identification of capsid domains involved in AAV-2-cell interaction and neutralization of AAV-2 infection," J Virol. 2000, 74(19), 9281-93.
Wu et al., "Effect of genome size on AAV vector packaging," Mol Ther., 2010, 18(1), 80-6.
Wu et al., "Optimization of self-complementary AAV vectors for liver-directed expression results in sustained correction of hemophilia B at low vector dose," Mol Ther., 2008, 16(2), 280-9.
Chuah et al. (2014) "Liver-Specific Transcriptional Modules Identified by Genome-Wide in Silico Analysis Enable Efficient Gene Therapy in Mice and Non-Human Primates" Molecular Therapy 22(9):1605-1613.
Dong et al. (1996) "Quantitative analysis of the packaging capacity of recombinant adeno-associated virus," Hum Gene Ther. 7(17):2101-12 (31 pages).
Harding et al. (2004) "Intravenous administration of an AA V-2 vector for the expression of factor IX in mice and a dog model of hemophilia B," Gene Ther. 11(2):204-13.
Loeb et al. (1999) "Enhanced expression of transgenes from adeno-associated virus vectors with the woodchuck hepatitis virus post-transcriptional regulatory element: implications for gene therapy," Hum Gene Ther. 10(14):2295-305.
McFarland et al. (2006) "Evaluation of a novel short polyadenylation signal as an alternative to the SV40 polyadenylation signal," Plasmid 56(1):62-7.
Murillo et al. (2016) "Improvement of Gene Therapy for Wilson Disease," Molecular Therapy 24(1)S64.
NCBI GenBank Accession No. U03464.1, Human P-type ATPase ATP7B mRNA, complete cds, Apr. 23, 1997 (3 pages).
NCBI Reference Sequence: NP_000044.2 copper-transporting ATPase 2 isoform a [*Homo sapiens*], Dec. 2, 2018 (5 pages).
Samadani et al. (1996) "Identification of a transthyretin enhancer site that selectively binds the hepatocyte nuclear factor-3 beta isoform," Gene Expr. 6(1):23-33.
Shanmugavel et al., "Probing functional roles of Wilson disease protein (ATP7B) Copper-binding domains in yeast," Metallomics, 2017, 9(7), 981-988, supplemental information (17 pages).
Valencia et al. (2008) Splicing promotes rapid and efficient mRNA export in mammalian cells, Proc Natl Acad Sci U S A. 105(9):3386-91.
Yan et al. (2012) "Human thyroxine binding globulin (TBG) promoter directs efficient and sustaining transgene expression in liver-specific pattern," Gene 506(2):289-94.

* cited by examiner

SEQUENCE LISTING

```
<160> NUMBER OF SEQ ID NOS: 15

<210> SEQ ID NO 1
<211> LENGTH: 3603
<212> TYPE: DNA
<213> ORGANISM: Artificial Sequence
<220> FEATURE:
<223> OTHER INFORMATION: Description of artificial sequence: Del 1-3
      ATP7B, native
<220> FEATURE:
<221> NAME/KEY: misc_feature
<222> LOCATION: (223)..(225)
<223> OTHER INFORMATION: Nucleotides 223-225 encode for serine residue
      S340 (numbering based on wild-type protein sequence)
<220> FEATURE:
<221> NAME/KEY: misc_feature
<222> LOCATION: (226)..(228)
<223> OTHER INFORMATION: Nucleotides 226-228 encode for serine residue
      S341 (numbering based on wild-type protein sequence)

<400> SEQUENCE: 1
atgcctgagc aggagagaca gatcacagcc agagaagggg ccagtcggaa aatcttatct      60
aagctttctt tgcctacccg tgcctgggaa ccagcaatga agaagagttt tgcttttgac     120
aatgttggct atgaaggtgg tctggatggc ctgggccctt cttctcaggt ggccaccagc     180
acagtcaggg atggagccga agggagtggg acagatcaca ggtcttccag ttctcattcc     240
cctggctccc caccgagaaa ccaggtccag ggcacatgca gtaccactct gattgccatt     300
gccggcatga cctgtgcatc ctgtgtccat tccattgaag gcatgatctc ccaactggaa     360
ggggtgcagc aaatatcggt gtctttggcc gaagggactg caacagttct ttataatccc     420
tctgtaatta gcccagaaga actcagagct gctagaaag acatgggatt tgaggcttca     480
gtcgtttctg aaagctgttc tactaaccct cttggaaacc acagtgctgg gaattccatg     540
gtgcaaacta cagatggtac acctacatct gtgcaggaag tggctcccca cactgggagg     600
ctccctgcaa accatgcccc ggacatcttg gcaaagtccc cacaatcaac cagagcagtg     660
gcaccgcaga agtgcttctt acagatcaaa ggcatgacct gtgcatcctg tgtgtctaac     720
atagaaagga atctgcagaa agaagctggt gttctctccg tgttggttgc cttgatggca     780
ggaaaggcag agatcaagta tgacccagag gtcatccagc ccctcgagat agctcagttc     840
atccaggacc tgggttttga ggcagcagtc atggaggact acgcaggctc cgatggcaac     900
attgagctga caatcacagg gatgacctgc gcgtcctgtg tccacaacat agagtccaaa     960
ctcacgagga caaatggcat cacttatgcc tccgttgccc ttgccaccag caaagccctt    1020
gttaagtttg acccggaaat tatcggtcca cgggatatta tcaaaattat tgaggaaatt    1080
ggctttcatg cttccctggc ccagagaaac cccaacgctc atcacttgga ccacaagatg    1140
gaaataaagc agtggaagaa gtcttttcctg tgcagcctgg tgtttggcat ccctgtcatg    1200
gccttaatga tctatatgct gataccccagc aacgagcccc accagtccat ggtcctggac    1260
```

```
cacaacatca ttccaggact gtccattcta aatctcatct tctttatctt gtgtaccttt    1320
gtccagctcc tcggtgggtg gtacttctac gttcaggcct acaaatctct gagacacagg    1380
tcagccaaca tggacgtgct catcgtcctg ccacaagca ttgcttatgt ttattctctg    1440
gtcatcctgg tggttgctgt ggctgagaag gcggagagga ccctgtgac attcttcgac    1500 acgcccccca tgctctttgt gttcattgcc ctgggccggt ggctggaaca cttggcaaag    1560
agcaaaacct cagaagccct ggctaaactc atgtctctcc aagccacaga agccaccgtt    1620
gtgacccttg gtgaggacaa tttaatcatc agggaggagc aagtccccat ggagctggtg    1680
cagcggggcg atatcgtcaa ggtggtccct gggggaaagt ttccagtgga tgggaaagtc    1740
ctggaaggca ataccatggc tgatgagtcc ctcatcacag gagaagccat gccagtcact    1800
aagaaacccg gaagcactgt aattgcgggg tctataaatg cacatggctc tgtgctcatt    1860
aaagctaccc acgtgggcaa tgacaccact ttggctcaga ttgtgaaact ggtggaagag    1920
gctcagatgt caaaggcacc cattcagcag ctggctgacc ggtttagtgg atattttgtc    1980
ccatttatca tcatcatgtc aactttgacg ttggtggtat ggattgtaat cggttttatc    2040
gattttggtg ttgttcagag atactttcct aaccccaaca agcacatctc ccagacagag    2100
gtgatcatcc ggtttgcttt ccagacgtcc atcacggtgc tgtgcattgc ctgcccctgc    2160
tccctggggc tggccacgcc cacggctgtc atggtgggca ccggggtggc cgcgcagaac    2220
ggcatcctca tcaagggagg caagcccctg gagatgcgcg caagataaa gactgtgatg    2280 tttgacaaga ctggcaccat tacccatggc gtccccaggg tcatgcgggt gctcctgctg    2340
ggggatgtgg ccacactgcc cctcaggaag gttctggctg tggtggggac tgcggaggcc    2400
agcagtgaac accccttggg cgtggcagtc accaaatact gtaaagagga acttggaaca    2460
gagaccttgg gatactgcac ggacttccag gcagtgccag gctgtggaat tgggtgcaaa    2520
gtcagcaacg tggaaggcat cctggcccac agtgagcgcc ctttgagtgc accggccagt    2580
cacctgaatg aggctggcag ccttcccgca gaaaaagatg cagtccccca gaccttctct    2640
gtgctgattg aaaccgtga gtggctgagg cgcaacggtt taaccatttc tagcgatgtc    2700
agtgacgcta tgacagacca cgagatgaaa ggacagacag ccatcctggt ggctattgac    2760
ggtgtgctct gtgggatgat cgcaatcgca gacgctgtca gcaggaggc tgccctggct    2820 gtgcacacgc tgcagagcat gggtgtggac gtggttctga tcacggggga caaccggaag    2880
acagccagag ctattgccac ccaggttggc atcaacaaag tctttgcaga ggtgctgcct    2940
tcgcacaagg tggccaaggt ccaggagctc cagaataaag ggaagaaagt cgccatggtg    3000 gggatgggg tcaatgactc cccggccttg gcccaggcag acatgggtgt ggccattggc    3060
accggcacgg atgtggccat cgaggcagcc gacgtcgtcc ttatcagaaa tgatttgctg    3120
gatgtggtgg ctagcattca cctttccaag aggactgtcc gaaggatacg catcaacctg    3180
gtcctggcac tgatttataa cctggttggg ataccccattg cagcaggtgt cttcatgccc    3240
atcggcattg tgctgcagcc ctggatgggc tcagcggcca tggcagcctc ctctgtgtct    3300
gtggtgctct catccctgca gctcaagtgc tataagaagc ctgacctgga gaggtatgag    3360
gcacaggcgc atgccacat gaagcccctg acggcatccc aggtcagtgt gcacataggc    3420
atggatgaca ggtggcggga ctccccccagg gccacaccat gggaccaggt cagctatgtc    3480
agccaggtgt cgctgtccct cctgacgtcc gacaagccat ctcggcacag cgctgcagca    3540
gacgatgatg gggacaagtg gtctctgctc ctgaatggca gggatgagga gcagtacatc    3600
tga                                                                   3603
```

<210> SEQ ID NO 2
<211> LENGTH: 145
<212> TYPE: DNA
<213> ORGANISM: Artificial Sequence
<220> FEATURE:
<223> OTHER INFORMATION: Description of artificial sequence: AAV2 ITR

<400> SEQUENCE: 2

```
ttggccactc cctctctgcg cgctcgctcg ctcactgagg ccgggcgacc aaaggtcgcc    60
cgacgcccgg gctttgcccg ggcggcctca gtgagcgagc gagcgcgcag agagggagtg   120
gccaactcca tcactagggg ttcct                                         145
```

<210> SEQ ID NO 3
<211> LENGTH: 100
<212> TYPE: DNA
<213> ORGANISM: Artificial Sequence
<220> FEATURE:
<223> OTHER INFORMATION: Description of artificial sequence: enTTR
      Enhancer sequence

<400> SEQUENCE: 3

```
ctacctcgtg atcgcccggc ccctgttcaa acatgtccta atactctgtc tctgcaaggg    60
tcatcagtag ttttccatct tactcaacat cctcccagtg                         100
```

<210> SEQ ID NO 4
<211> LENGTH: 95
<212> TYPE: DNA
<213> ORGANISM: Artificial Sequence
<220> FEATURE:
<223> OTHER INFORMATION: Description of artificial sequence: SV40 Small
      T Intron

<400> SEQUENCE: 4

```
gctctaaggt aaatataaaa ttttaagtg tataatgtgt taaactactg attctaattg     60
tttctctctt ttagattcca acctttggaa ctgat                               95
```

<210> SEQ ID NO 5
<211> LENGTH: 315
<212> TYPE: DNA
<213> ORGANISM: Artificial Sequence
<220> FEATURE:
<223> OTHER INFORMATION: Description of artificial sequence: rHBB Intron

<400> SEQUENCE: 5

```
gtgagcgggc gggacggccc ttctcctccg ggctgtaatt agcgcttggt ttaatgacgg    60
cttgtttctt ttctgtggct gcgtgaaagc cttgaggggc tccgggaggg ccctttgtgc   120 gggggggagcg gctcggggct gtccgcgggg ggacggctgc cttcgggggg gacggggcag   180
ggcggggttc ggcttctggc gtgtgaccgg cggctcaaga gcctctgcta accatgttca   240
tgccttcttc ttttttcctac agctcctggg caacgtgctg gttattgtgc tgtctcatca   300
ttttggcaaa gaatt                                                    315
```

<210> SEQ ID NO 6
<211> LENGTH: 215
<212> TYPE: DNA
<213> ORGANISM: Artificial Sequence
<220> FEATURE:
<223> OTHER INFORMATION: Description of artificial sequence: BGH
      polyadenylation signal sequence

<400> SEQUENCE: 6
gcctcgactg tgccttctag ttgccagcca tctgttgttt gccctcccc cgtgccttcc     60 ttgaccctgg aaggtgccac tcccactgtc ctttcctaat aaaatgagga aattgcatcg    120
cattgtctga gtaggtgtca ttctattctg ggggtgggg tggggcagga cagcaagggg    180
gaggattggg aagacaatag caggcatgct gggga                              215

<210> SEQ ID NO 7
<211> LENGTH: 198
<212> TYPE: DNA
<213> ORGANISM: Artificial Sequence
<220> FEATURE:
<223> OTHER INFORMATION: Description of artificial sequence: SV40
      polyadenylation signal sequence

<400> SEQUENCE: 7
gatccagaca tgataagata cattgatgag tttggacaaa ccacaactag aatgcagtga     60
aaaaaatgct ttatttgtga aatttgtgat gctattgctt tatttgtaac cattataagc    120
tgcaataaac aagttaacaa caacaattgc attcatttta tgtttcaggt tcaggggag    180 gtgtgggagg ttttttag                                                 198

<210> SEQ ID NO 8
<211> LENGTH: 1200
<212> TYPE: PRT
<213> ORGANISM: Artificial Sequence
<220> FEATURE:
<223> OTHER INFORMATION: Description of artificial sequence: DEL 1-3
      ATP7B Native, protein
<220> FEATURE:
<221> NAME/KEY: MISC_FEATURE
<222> LOCATION: (75)..(75)
<223> OTHER INFORMATION: Amino acid residue at position 75 corresponds
      to Serine S340 (numbering based on wild-type protein sequence)
<220> FEATURE:
<221> NAME/KEY: MISC_FEATURE
<222> LOCATION: (76)..(76)
<223> OTHER INFORMATION: Amino acid residue at position 76 corresponds
      to Serine S341 (numbering based on wild-type protein sequence)

<400> SEQUENCE: 8

Met Pro Glu Gln Glu Arg Gln Ile Thr Ala Arg Glu Gly Ala Ser Arg
1               5                   10                  15

Lys Ile Leu Ser Lys Leu Ser Leu Pro Thr Arg Ala Trp Glu Pro Ala
            20                  25                  30

Met Lys Lys Ser Phe Ala Phe Asp Asn Val Gly Tyr Glu Gly Gly Leu
        35                  40                  45

Asp Gly Leu Gly Pro Ser Ser Gln Val Ala Thr Ser Thr Val Arg Asp
    50                  55                  60

Gly Ala Glu Gly Ser Gly Thr Asp His Arg Ser Ser Ser His Ser
65                  70                  75                  80

Pro Gly Ser Pro Pro Arg Asn Gln Val Gln Gly Thr Cys Ser Thr Thr
                85                  90                  95

Leu Ile Ala Ile Ala Gly Met Thr Cys Ala Ser Cys Val His Ser Ile
            100                 105                 110

Glu Gly Met Ile Ser Gln Leu Glu Gly Val Gln Gln Ile Ser Val Ser
        115                 120                 125

Leu Ala Glu Gly Thr Ala Thr Val Leu Tyr Asn Pro Ser Val Ile Ser
    130                 135                 140

Pro Glu Glu Leu Arg Ala Ala Ile Glu Asp Met Gly Phe Glu Ala Ser
145                 150                 155                 160

-continued

Val Val Ser Glu Ser Cys Ser Thr Asn Pro Leu Gly Asn His Ser Ala
                165                 170                 175

Gly Asn Ser Met Val Gln Thr Thr Asp Gly Thr Pro Thr Ser Val Gln
            180                 185                 190

Glu Val Ala Pro His Thr Gly Arg Leu Pro Ala Asn His Ala Pro Asp
        195                 200                 205

Ile Leu Ala Lys Ser Pro Gln Ser Thr Arg Ala Val Ala Pro Gln Lys
    210                 215                 220

Cys Phe Leu Gln Ile Lys Gly Met Thr Cys Ala Ser Cys Val Ser Asn
225                 230                 235                 240

Ile Glu Arg Asn Leu Gln Lys Glu Ala Gly Val Leu Ser Val Leu Val
                245                 250                 255

Ala Leu Met Ala Gly Lys Ala Glu Ile Lys Tyr Asp Pro Glu Val Ile
            260                 265                 270

Gln Pro Leu Glu Ile Ala Gln Phe Ile Gln Asp Leu Gly Phe Glu Ala
        275                 280                 285

Ala Val Met Glu Asp Tyr Ala Gly Ser Asp Gly Asn Ile Glu Leu Thr
    290                 295                 300

Ile Thr Gly Met Thr Cys Ala Ser Cys Val His Asn Ile Glu Ser Lys
305                 310                 315                 320

Leu Thr Arg Thr Asn Gly Ile Thr Tyr Ala Ser Val Ala Leu Ala Thr
                325                 330                 335

Ser Lys Ala Leu Val Lys Phe Asp Pro Glu Ile Ile Gly Pro Arg Asp
            340                 345                 350

Ile Ile Lys Ile Ile Glu Glu Ile Gly Phe His Ala Ser Leu Ala Gln
        355                 360                 365

Arg Asn Pro Asn Ala His His Leu Asp His Lys Met Glu Ile Lys Gln
    370                 375                 380

Trp Lys Lys Ser Phe Leu Cys Ser Leu Val Phe Gly Ile Pro Val Met
385                 390                 395                 400

Ala Leu Met Ile Tyr Met Leu Ile Pro Ser Asn Glu Pro His Gln Ser
                405                 410                 415

Met Val Leu Asp His Asn Ile Ile Pro Gly Leu Ser Ile Leu Asn Leu
            420                 425                 430

Ile Phe Phe Ile Leu Cys Thr Phe Val Gln Leu Leu Gly Gly Trp Tyr
        435                 440                 445

Phe Tyr Val Gln Ala Tyr Lys Ser Leu Arg His Arg Ser Ala Asn Met
    450                 455                 460

Asp Val Leu Ile Val Leu Ala Thr Ser Ile Ala Tyr Val Tyr Ser Leu
465                 470                 475                 480

Val Ile Leu Val Val Ala Val Ala Glu Lys Ala Glu Arg Ser Pro Val
                485                 490                 495

Thr Phe Phe Asp Thr Pro Pro Met Leu Phe Val Phe Ile Ala Leu Gly
            500                 505                 510

Arg Trp Leu Glu His Leu Ala Lys Ser Lys Thr Ser Glu Ala Leu Ala
        515                 520                 525

Lys Leu Met Ser Leu Gln Ala Thr Glu Ala Thr Val Val Thr Leu Gly
    530                 535                 540

Glu Asp Asn Leu Ile Ile Arg Glu Glu Gln Val Pro Met Glu Leu Val
545                 550                 555                 560

Gln Arg Gly Asp Ile Val Lys Val Val Pro Gly Gly Lys Phe Pro Val
                565                 570                 575

Asp Gly Lys Val Leu Glu Gly Asn Thr Met Ala Asp Glu Ser Leu Ile

```
            580             585             590
Thr Gly Glu Ala Met Pro Val Thr Lys Lys Pro Gly Ser Thr Val Ile
            595             600             605
Ala Gly Ser Ile Asn Ala His Gly Ser Val Leu Ile Lys Ala Thr His
            610             615             620
Val Gly Asn Asp Thr Thr Leu Ala Gln Ile Val Lys Leu Val Glu Glu
625             630             635             640
Ala Gln Met Ser Lys Ala Pro Ile Gln Gln Leu Ala Asp Arg Phe Ser
            645             650             655
Gly Tyr Phe Val Pro Phe Ile Ile Met Ser Thr Leu Thr Leu Val
            660             665             670
Val Trp Ile Val Ile Gly Phe Ile Asp Phe Gly Val Val Gln Arg Tyr
            675             680             685
Phe Pro Asn Pro Asn Lys His Ile Ser Gln Thr Glu Val Ile Ile Arg
            690             695             700
Phe Ala Phe Gln Thr Ser Ile Thr Val Leu Cys Ile Ala Cys Pro Cys
705             710             715             720
Ser Leu Gly Leu Ala Thr Pro Thr Ala Val Met Val Gly Thr Gly Val
            725             730             735
Ala Ala Gln Asn Gly Ile Leu Ile Lys Gly Gly Lys Pro Leu Glu Met
            740             745             750
Ala His Lys Ile Lys Thr Val Met Phe Asp Lys Thr Gly Thr Ile Thr
            755             760             765
His Gly Val Pro Arg Val Met Arg Val Leu Leu Leu Gly Asp Val Ala
            770             775             780
Thr Leu Pro Leu Arg Lys Val Leu Ala Val Val Gly Thr Ala Glu Ala
785             790             795             800
Ser Ser Glu His Pro Leu Gly Val Ala Val Thr Lys Tyr Cys Lys Glu
            805             810             815
Glu Leu Gly Thr Glu Thr Leu Gly Tyr Cys Thr Asp Phe Gln Ala Val
            820             825             830
Pro Gly Cys Gly Ile Gly Cys Lys Val Ser Asn Val Glu Gly Ile Leu
            835             840             845
Ala His Ser Glu Arg Pro Leu Ser Ala Pro Ala Ser His Leu Asn Glu
850             855             860
Ala Gly Ser Leu Pro Ala Glu Lys Asp Ala Val Pro Gln Thr Phe Ser
865             870             875             880
Val Leu Ile Gly Asn Arg Glu Trp Leu Arg Arg Asn Gly Leu Thr Ile
            885             890             895
Ser Ser Asp Val Ser Asp Ala Met Thr Asp His Glu Met Lys Gly Gln
            900             905             910
Thr Ala Ile Leu Val Ala Ile Asp Gly Val Leu Cys Gly Met Ile Ala
            915             920             925
Ile Ala Asp Ala Val Lys Gln Glu Ala Ala Leu Ala Val His Thr Leu
            930             935             940
Gln Ser Met Gly Val Asp Val Leu Ile Thr Gly Asp Asn Arg Lys
945             950             955             960
Thr Ala Arg Ala Ile Ala Thr Gln Val Gly Ile Asn Lys Val Phe Ala
            965             970             975
Glu Val Leu Pro Ser His Lys Val Ala Lys Val Gln Glu Leu Gln Asn
            980             985             990
Lys Gly Lys Lys Val Ala Met Val  Gly Asp Gly Val Asn  Asp Ser Pro
            995             1000             1005
```

```
Ala Leu Ala Gln Ala Asp Met Gly Val Ala Ile Gly Thr Gly Thr
    1010                1015                1020

Asp Val Ala Ile Glu Ala Ala Asp Val Val Leu Ile Arg Asn Asp
    1025                1030                1035

Leu Leu Asp Val Val Ala Ser Ile His Leu Ser Lys Arg Thr Val
    1040                1045                1050

Arg Arg Ile Arg Ile Asn Leu Val Leu Ala Leu Ile Tyr Asn Leu
    1055                1060                1065

Val Gly Ile Pro Ile Ala Ala Gly Val Phe Met Pro Ile Gly Ile
    1070                1075                1080

Val Leu Gln Pro Trp Met Gly Ser Ala Ala Met Ala Ala Ser Ser
    1085                1090                1095

Val Ser Val Val Leu Ser Ser Leu Gln Leu Lys Cys Tyr Lys Lys
    1100                1105                1110

Pro Asp Leu Glu Arg Tyr Glu Ala Gln Ala His Gly His Met Lys
    1115                1120                1125

Pro Leu Thr Ala Ser Gln Val Ser Val His Ile Gly Met Asp Asp
    1130                1135                1140

Arg Trp Arg Asp Ser Pro Arg Ala Thr Pro Trp Asp Gln Val Ser
    1145                1150                1155

Tyr Val Ser Gln Val Ser Leu Ser Ser Leu Thr Ser Asp Lys Pro
    1160                1165                1170

Ser Arg His Ser Ala Ala Ala Asp Asp Gly Asp Lys Trp Ser
    1175                1180                1185

Leu Leu Leu Asn Gly Arg Asp Glu Glu Gln Tyr Ile
    1190                1195                1200

<210> SEQ ID NO 9
<211> LENGTH: 2211
<212> TYPE: DNA
<213> ORGANISM: Artificial Sequence
<220> FEATURE:
<223> OTHER INFORMATION: Description of artificial sequence: Nucleic
      acid sequence encoding AAV9 capsid protein VP1

<400> SEQUENCE: 9
atggctgccg atggttatct tccagattgg ctcgaggaca accttagtga aggaattcgc      60
gagtggtggg cttgaaacc tggagcccct caacccaagg caaatcaaca acatcaagac     120
aacgctcgag gtcttgtgct tccgggttac aaataccttg acccggcaa cggactcgac      180 aaggggagc cggtcaacgc agcagacgcg gcggccctcg agcacgacaa ggcctacgac      240
cagcagctca aggccggaga caacccgtac ctcaagtaca ccacgccga cgccgagttc      300 caggagcggc tcaaagaaga tacgtctttt gggggcaacc tcgggcgagc agtcttccag      360
gccaaaaaga ggcttcttga acctcttggt ctggttgagg aagcggctaa cggctcct      420 ggaaagaaga ggcctgtaga gcagtctcct caggaaccgg actcctccgc gggtattggc      480
aaatcgggtg cacagcccgc taaaaagaga ctcaatttcg gtcagactgg cgacacagag      540
tcagtcccag accctcaacc aatcggagaa cctcccgcag cccctcagg tgtgggatct      600 cttacaatgg cttcaggtgg tggcgcacca gtggcagaca taacgaagg tgccgatgga      660 gtgggtagtt cctcgggaaa ttggcattgc gattcccaat ggctggggga cagagtcatc      720
accaccagca cccgaacctg ggccctgccc acctacaaca tcacctcta caagcaaatc      780 tccaacagca catctggagg atcttcaat gacaacgcct acttcggcta cagcaccccc      840
```

```
tgggggtatt ttgacttcaa cagattccac tgccacttct caccacgtga ctggcagcga    900
ctcatcaaca acaactgggg attccggcct aagcgactca acttcaagct cttcaacatt    960
caggtcaaag aggttacgga caacaatgga gtcaagacca tcgccaataa ccttaccagc   1020
acggtccagg tcttcacgga ctcagactat cagctcccgt acgtgctcgg tcgggctcac   1080
gagggctgcc tcccgccgtt cccagcggac gttttcatga ttcctcagta cgggtatctg   1140
acgcttaatg atggaagcca ggccgtgggt cgttcgtcct tttactgcct ggaatatttc   1200
ccgtcgcaaa tgctaagaac gggtaacaac ttccagttca gctacgagtt tgagaacgta   1260
cctttccata gcagctacgc tcacagccaa agcctggacc gactaatgaa tccactcatc   1320
gaccaatact tgtactatct ctcaaagact attaacggtt ctggacagaa tcaacaaacg   1380
ctaaaattca gtgtggccgg acccagcaac atggctgtcc agggaagaaa ctacatacct   1440
ggacccagct accgacaaca acgtgtctca accactgtga ctcaaaacaa caacagcgaa   1500
tttgcttggc ctggagcttc ttcttgggct ctcaatggac gtaatagctt gatgaatcct   1560
ggacctgcta tggccagcca caagaaggag gaggaccgtt tctttccttt gtctggatct   1620
ttaattttg gcaaacaagg aactggaaga gacaacgtgg atgcggacaa agtcatgata   1680
accaacgaag aagaaattaa aactactaac ccggtagcaa cggagtccta tggacaagtg   1740
gccacaaacc accagagtgc ccaagcacag gcgcagaccg gctgggttca aaaccaagga   1800
atacttccgg gtatggtttg caggacagag atgtgtacc tgcaaggacc catttgggcc   1860
aaaattcctc acacggacgg caactttcac ccttctccgc tgatgggagg gtttggaatg   1920
aagcacccgc ctcctcagat cctcatcaaa aacacacctg tacctgcgga tcctccaacg   1980
gccttcaaca aggacaagct gaactctttc atcacccagt attctactgg ccaagtcagc   2040
gtggagatcg agtgggagct gcagaaggaa acagcaagc gctggaaccc ggagatccag   2100
tacacttcca actattacaa gtctaataat gttgaatttg ctgttaatac tgaaggtgta   2160
tatagtgaac cccgccccat tggcaccaga tacctgactc gtaatctgta a             2211
```

<210> SEQ ID NO 10
<211> LENGTH: 736
<212> TYPE: PRT
<213> ORGANISM: Artificial Sequence
<220> FEATURE:
<223> OTHER INFORMATION: Description of artificial sequence: Amino acid
      sequence encoding AAV9 capsid protein VP1

<400> SEQUENCE: 10

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
```

```
            115                 120                 125
Leu Gly Leu Val Glu Ala Ala Lys Thr Ala Pro Gly Lys Lys Arg
        130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
                195                 200                 205
Ala Pro Val Ala Asp Asn Asn Glu Gly Ala Asp Gly Val Gly Ser Ser
        210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Ser Ser Asn Asp Asn
                260                 265                 270
Ala Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
        290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
            355                 360                 365
Ala Asp Val Phe Met Ile Pro Gln Tyr Gly Tyr Leu Thr Leu Asn Asp
        370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
        450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
        530                 535                 540
```

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 11
<211> LENGTH: 6
<212> TYPE: DNA
<213> ORGANISM: Artificial Sequence
<220> FEATURE:
<223> OTHER INFORMATION: Description of artificial sequence: Consensus
      Kozak Sequence

<400> SEQUENCE: 11 gccgcc                                                                   6

<210> SEQ ID NO 12
<211> LENGTH: 190
<212> TYPE: DNA
<213> ORGANISM: Artificial Sequence
<220> FEATURE:
<223> OTHER INFORMATION: Description of artificial sequence: TTR
      promoter Sequence

<400> SEQUENCE: 12
atttcataga acgaatgttc cgatgctcta atctctctag acaaggttca tatttgtatg        60
ggttacttat tctctctttg ttgactaagt caataatcag aatcagcagg tttgcagtca       120
gattggcagg gataagcagc ctagctcagg agaagtgagt ataaaagccc caggctggga       180
gcagccatca                                                              190

<210> SEQ ID NO 13
<211> LENGTH: 1120
<212> TYPE: PRT
<213> ORGANISM: Artificial Sequence
<220> FEATURE:
<223> OTHER INFORMATION: Description of artificial sequence: DEL 1-4
      ATP7B Native, protein

<400> SEQUENCE: 13

-continued

```
Met Pro Glu Gln Glu Arg Gln Ile Thr Ala Arg Gly Ala Ser Arg
1               5                   10                  15

Lys Ile Leu Ser Lys Leu Ser Leu Pro Thr Arg Ala Trp Glu Pro Ala
                20                  25                  30

Met Lys Lys Ser Phe Ala Phe Asp Asn Val Gly Tyr Glu Gly Gly Leu
            35                  40                  45

Asp Gly Leu Gly Pro Ser Ser Gln Val Ala Thr Ser Thr Val Arg Ser
        50                  55                  60

Pro Glu Glu Leu Arg Ala Ala Ile Glu Asp Met Gly Phe Glu Ala Ser
65                  70                  75                  80

Val Val Ser Glu Ser Cys Ser Thr Asn Pro Leu Gly Asn His Ser Ala
                85                  90                  95

Gly Asn Ser Met Val Gln Thr Thr Asp Gly Thr Pro Thr Ser Val Gln
            100                 105                 110

Glu Val Ala Pro His Thr Gly Arg Leu Pro Ala Asn His Ala Pro Asp
        115                 120                 125

Ile Leu Ala Lys Ser Pro Gln Ser Thr Arg Ala Val Ala Pro Gln Lys
        130                 135                 140

Cys Phe Leu Gln Ile Lys Gly Met Thr Cys Ala Ser Cys Val Ser Asn
145                 150                 155                 160

Ile Glu Arg Asn Leu Gln Lys Glu Ala Gly Val Leu Ser Val Leu Val
                165                 170                 175

Ala Leu Met Ala Gly Lys Ala Glu Ile Lys Tyr Asp Pro Glu Val Ile
            180                 185                 190

Gln Pro Leu Glu Ile Ala Gln Phe Ile Gln Asp Leu Gly Phe Glu Ala
        195                 200                 205

Ala Val Met Glu Asp Tyr Ala Gly Ser Asp Gly Asn Ile Glu Leu Thr
        210                 215                 220

Ile Thr Gly Met Thr Cys Ala Ser Cys Val His Asn Ile Glu Ser Lys
225                 230                 235                 240

Leu Thr Arg Thr Asn Gly Ile Thr Tyr Ala Ser Val Ala Leu Ala Thr
                245                 250                 255

Ser Lys Ala Leu Val Lys Phe Asp Pro Glu Ile Ile Gly Pro Arg Asp
            260                 265                 270

Ile Ile Lys Ile Ile Glu Glu Ile Gly Phe His Ala Ser Leu Ala Gln
        275                 280                 285

Arg Asn Pro Asn Ala His His Leu Asp His Lys Met Glu Ile Lys Gln
        290                 295                 300

Trp Lys Lys Ser Phe Leu Cys Ser Leu Val Phe Gly Ile Pro Val Met
305                 310                 315                 320

Ala Leu Met Ile Tyr Met Leu Ile Pro Ser Asn Glu Pro His Gln Ser
            325                 330                 335

Met Val Leu Asp His Asn Ile Ile Pro Gly Leu Ser Ile Leu Asn Leu
        340                 345                 350

Ile Phe Phe Ile Leu Cys Thr Phe Val Gln Leu Leu Gly Gly Trp Tyr
        355                 360                 365

Phe Tyr Val Gln Ala Tyr Lys Ser Leu Arg His Arg Ser Ala Asn Met
        370                 375                 380

Asp Val Leu Ile Val Leu Ala Thr Ser Ile Ala Tyr Val Tyr Ser Leu
385                 390                 395                 400

Val Ile Leu Val Val Ala Val Ala Glu Lys Ala Glu Arg Ser Pro Val
                405                 410                 415
```

```
Thr Phe Phe Asp Thr Pro Pro Met Leu Phe Val Phe Ile Ala Leu Gly
                420                 425                 430

Arg Trp Leu Glu His Leu Ala Lys Ser Lys Thr Ser Glu Ala Leu Ala
        435                 440                 445

Lys Leu Met Ser Leu Gln Ala Thr Glu Ala Thr Val Val Thr Leu Gly
        450                 455                 460

Glu Asp Asn Leu Ile Ile Arg Glu Glu Gln Val Pro Met Glu Leu Val
465                 470                 475                 480

Gln Arg Gly Asp Ile Val Lys Val Val Pro Gly Gly Lys Phe Pro Val
                485                 490                 495

Asp Gly Lys Val Leu Glu Gly Asn Thr Met Ala Asp Glu Ser Leu Ile
                500                 505                 510

Thr Gly Glu Ala Met Pro Val Thr Lys Lys Pro Gly Ser Thr Val Ile
        515                 520                 525

Ala Gly Ser Ile Asn Ala His Gly Ser Val Leu Ile Lys Ala Thr His
        530                 535                 540

Val Gly Asn Asp Thr Thr Leu Ala Gln Ile Val Lys Leu Val Glu Glu
545                 550                 555                 560

Ala Gln Met Ser Lys Ala Pro Ile Gln Gln Leu Ala Asp Arg Phe Ser
                565                 570                 575

Gly Tyr Phe Val Pro Phe Ile Ile Met Ser Thr Leu Thr Leu Val
        580                 585                 590

Val Trp Ile Val Ile Gly Phe Ile Asp Phe Gly Val Val Gln Arg Tyr
        595                 600                 605

Phe Pro Asn Pro Asn Lys His Ile Ser Gln Thr Glu Val Ile Ile Arg
610                 615                 620

Phe Ala Phe Gln Thr Ser Ile Thr Val Leu Cys Ile Ala Cys Pro Cys
625                 630                 635                 640

Ser Leu Gly Leu Ala Thr Pro Thr Ala Val Met Val Gly Thr Gly Val
                645                 650                 655

Ala Ala Gln Asn Gly Ile Leu Ile Lys Gly Gly Lys Pro Leu Glu Met
                660                 665                 670

Ala His Lys Ile Lys Thr Val Met Phe Asp Lys Thr Gly Thr Ile Thr
        675                 680                 685

His Gly Val Pro Arg Val Met Arg Val Leu Leu Leu Gly Asp Val Ala
        690                 695                 700

Thr Leu Pro Leu Arg Lys Val Leu Ala Val Val Gly Thr Ala Glu Ala
705                 710                 715                 720

Ser Ser Glu His Pro Leu Gly Val Ala Val Thr Lys Tyr Cys Lys Glu
                725                 730                 735

Glu Leu Gly Thr Glu Thr Leu Gly Tyr Cys Thr Asp Phe Gln Ala Val
                740                 745                 750

Pro Gly Cys Gly Ile Gly Cys Lys Val Ser Asn Val Glu Gly Ile Leu
        755                 760                 765

Ala His Ser Glu Arg Pro Leu Ser Ala Pro Ala Ser His Leu Asn Glu
        770                 775                 780

Ala Gly Ser Leu Pro Ala Glu Lys Asp Ala Val Pro Gln Thr Phe Ser
785                 790                 795                 800

Val Leu Ile Gly Asn Arg Glu Trp Leu Arg Arg Asn Gly Leu Thr Ile
                805                 810                 815

Ser Ser Asp Val Ser Asp Ala Met Thr Asp His Glu Met Lys Gly Gln
                820                 825                 830

Thr Ala Ile Leu Val Ala Ile Asp Gly Val Leu Cys Gly Met Ile Ala
```

Ile Ala Asp Ala Val Lys Gln Glu Ala Ala Leu Ala Val His Thr Leu
835                 840                 845

Gln Ser Met Gly Val Asp Val Leu Ile Thr Gly Asp Asn Arg Lys
850                 855                 860

Thr Ala Arg Ala Ile Ala Thr Gln Val Gly Ile Asn Lys Val Phe Ala
865                 870                 875                 880

Glu Val Leu Pro Ser His Lys Val Ala Lys Val Gln Glu Leu Gln Asn
    885                 890                 895

Lys Gly Lys Lys Val Ala Met Val Gly Asp Gly Val Asn Asp Ser Pro
900                 905                 910

Ala Leu Ala Gln Ala Asp Met Gly Val Ala Ile Gly Thr Gly Thr Asp
915                 920                 925

Val Ala Ile Glu Ala Ala Asp Val Val Leu Ile Arg Asn Asp Leu Leu
930                 935                 940

Asp Val Val Ala Ser Ile His Leu Ser Lys Arg Thr Val Arg Arg Ile
945                 950                 955                 960

Arg Ile Asn Leu Val Leu Ala Leu Ile Tyr Asn Leu Val Gly Ile Pro
    965                 970                 975

Ile Ala Ala Gly Val Phe Met Pro Ile Gly Ile Val Leu Gln Pro Trp
980                 985                 990

Met Gly Ser Ala Ala Met Ala Ala Ser Ser Val Ser Val Val Leu
995                 1000                1005

Ser Ser Leu Gln Leu Lys Cys Tyr Lys Lys Pro Asp Leu Glu Arg
1010                1015                1020

Tyr Glu Ala Gln Ala His Gly His Met Lys Pro Leu Thr Ala Ser
1025                1030                1035

Gln Val Ser Val His Ile Gly Met Asp Asp Arg Trp Arg Asp Ser
1040                1045                1050

Pro Arg Ala Thr Pro Trp Asp Gln Val Ser Tyr Val Ser Gln Val
1055                1060                1065

Ser Leu Ser Ser Leu Thr Ser Asp Lys Pro Ser Arg His Ser Ala
1070                1075                1080

Ala Ala Asp Asp Asp Gly Asp Lys Trp Ser Leu Leu Leu Asn Gly
1085                1090                1095

Arg Asp Glu Glu Gln Tyr Ile
1100                1105                1110

1115                1120

<210> SEQ ID NO 14
<211> LENGTH: 4485
<212> TYPE: DNA
<213> ORGANISM: Artificial Sequence
<220> FEATURE:
<223> OTHER INFORMATION: Description of artificial sequence: Expression
      cassette of exemplary vector DTC319

<400> SEQUENCE: 14
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctctacc tcgtgatcgc ccggcccctg ttcaaacatg     180
tcctaatact ctgtctctgc aagggtcatc agtagttttc catcttactc aacatcctcc     240
cagtgatttc atagaacgaa tgttccgatg ctctaatctc tctagacaag gttcatattt     300
gtatgggtta cttattctct ctttgttgac taagtcaata atcagaatca gcaggtttgc     360

-continued

| | | |
|---|---|---|
| agtcagattg gcagggataa gcagcctagc tcaggagaag tgagtataaa agccccaggc | 420 |
| tgggagcagc catcagctct aaggtaaata taaaatttt aagtgtataa tgtgttaaac | 480 |
| tactgattct aattgtttct ctcttttaga ttccaacctt tggaactgat gccgccacca | 540 |
| tgcctgagca ggagagacag atcacagcca gagaaggggc cagtcggaaa atcttatcta | 600 |
| agctttcttt gcctacccgt gcctgggaac cagcaatgaa gaagagtttt gcttttgaca | 660 |
| atgttggcta tgaaggtggt ctggatggcc tgggcccttc ttctcaggtg gccaccagca | 720 |
| cagtcaggga tggagccgaa gggagtggga cagatcacag gtcttccagt tctcattccc | 780 |
| ctggctcccc accgagaaac caggtccagg gcacatgcag taccactctg attgccattg | 840 |
| ccggcatgac ctgtgcatcc tgtgtccatt ccattgaagg catgatctcc caactggaag | 900 |
| gggtgcagca aatatcggtg tctttggccg aagggactgc aacagttctt tataatccct | 960 |
| ctgtaattag cccagaagaa ctcagagctg ctatagaaga catgggattt gaggcttcag | 1020 |
| tcgtttctga agctgttct actaaccctc ttggaaacca cagtgctggg aattccatgg | 1080 |
| tgcaaactac agatggtaca cctacatctg tgcaggaagt ggctccccac actgggaggc | 1140 |
| tccctgcaaa ccatgccccg acatcttgg caaagtcccc acaatcaacc agagcagtgg | 1200 |
| caccgcagaa gtgcttctta cagatcaaag gcatgacctg tgcatcctgt gtgtctaaca | 1260 |
| tagaaaggaa tctgcagaaa gaagctggtg ttctctccgt gttggttgcc ttgatggcag | 1320 |
| gaaaggcaga gatcaagtat gacccagagg tcatccagcc cctcgagata gctcagttca | 1380 |
| tccaggacct gggttttgag gcagcagtca tggaggacta cgcaggctcc gatggcaaca | 1440 |
| ttgagctgac aatcacaggg atgacctgcg cgtcctgtgt ccacaacata gagtccaaac | 1500 |
| tcacgaggac aaatggcatc acttatgcct ccgttgccct tgccaccagc aaagcccttg | 1560 |
| ttaagtttga cccggaaatt atcggtccac gggatattat caaaattatt gaggaaattg | 1620 |
| gctttcatgc ttccctggcc cagagaaacc ccaacgctca tcacttggac cacaagatgg | 1680 |
| aaataaagca gtggaagaag tcttttcctgt gcagcctggt gtttggcatc cctgtcatgg | 1740 |
| ccttaatgat ctatatgctg atacccagca acgagcccca ccagtccatg gtcctggacc | 1800 |
| acaacatcat tccaggactg tccattctaa atctcatctt cttttatcctg tgtacctttg | 1860 |
| tccagctcct cggtgggtgg tacttctacg ttcaggccta caaatctctg agacacaggt | 1920 |
| cagccaacat ggacgtgctc atcgtcctgg ccacaagcat tgcttatgtt tattctctgg | 1980 |
| tcatcctggt ggttgctgtg gctgagaagg cggagaggag ccctgtgaca ttcttcgaca | 2040 |
| cgccccccat gctctttgtg ttcattgccc tgggccggtg gctggaacac ttggcaaaga | 2100 |
| gcaaaacctc agaagccctg gctaaactca tgtctctcca agccacagaa gccaccgttg | 2160 |
| tgacccttgg tgaggacaat ttaatcatca gggaggagca agtccccatg gagctggtgc | 2220 |
| agcgggggcga tatcgtcaag gtggtccctg ggggaaagtt tccagtggat gggaaagtcc | 2280 |
| tggaaggcaa taccatggct gatgagtccc tcatcacagg agaagccatg ccagtcacta | 2340 |
| agaaacccgg aagcactgta attgcggggt ctataaatgc acatggctct gtgctcatta | 2400 |
| aagctaccca cgtgggcaat gacaccactt tggctcagat tgtgaaactg gtggaagagg | 2460 |
| ctcagatgtc aaaggcaccc attcagcagc tggctgaccg gttagtggaa tattttgtcc | 2520 |
| catttatcat catcatgtca actttgacgt tggtggtatg gattgtaatc ggtttttatcg | 2580 |
| attttggtgt tgttcagaga tacttttccta accccaacaa gcacatctcc cagacagagg | 2640 |
| tgatcatccg gtttgctttc cagacgtcca tcacggtgct gtgcattgcc tgccctgct | 2700 |
| ccctgggggct ggccacgccc acggctgtca tggtgggcac cggggtggcc gcgcagaacg | 2760 |

| | |
|---|---|
| gcatcctcat caagggaggc aagcccctgg agatggcgca caagataaag actgtgatgt | 2820 |
| ttgacaagac tggcaccatt acccatggcg tccccagggt catgcgggtg ctcctgctgg | 2880 |
| gggatgtggc cacactgccc ctcaggaagg ttctggctgt ggtggggact gcggaggcca | 2940 |
| gcagtgaaca cccccttgggc gtggcagtca ccaaatactg taaagaggaa cttggaacag | 3000 |
| agaccttggg atactgcacg gacttccagg cagtgccagg ctgtggaatt gggtgcaaag | 3060 |
| tcagcaacgt ggaaggcatc ctggcccaca gtgagcgccc tttgagtgca ccggccagtc | 3120 |
| acctgaatga ggctggcagc cttcccgcag aaaaagatgc agtcccccag accttctctg | 3180 |
| tgctgattgg aaaccgtgag tggctgaggc gcaacggttt aaccatttct agcgatgtca | 3240 |
| gtgacgctat gacagaccac gagatgaaag acagacagc catcctggtg ctattgacg | 3300 |
| gtgtgctctg tgggatgatc gcaatcgcag acgctgtcaa gcaggaggct gccctggctg | 3360 |
| tgcacacgct gcagagcatg ggtgtggacg tggttctgat cacgggggac aaccggaaga | 3420 |
| cagccagagc tattgccacc caggttggca tcaacaaagt cttttgcagag gtgctgcctt | 3480 |
| cgcacaaggt ggccaaggtc caggagctcc agaataaagg gaagaaagtc gccatggtgg | 3540 |
| gggatggggt caatgactcc ccggccttgg cccaggcaga catgggtgtg gccattggca | 3600 |
| ccggcacgga tgtggccatc gaggcagccg acgtcgtcct tatcagaaat gatttgctgg | 3660 |
| atgtggtggc tagcattcac ctttccaaga ggactgtccg aaggatacgc atcaacctgg | 3720 |
| tcctggcact gatttataac ctggttggga tacccattgc agcaggtgtc ttcatgccca | 3780 |
| tcggcattgt gctgcagccc tggatgggct cagcggccat ggcagcctcc tctgtgtctg | 3840 |
| tggtgctctc atccctgcag ctcaagtgct ataagaagcc tgacctggag aggtatgagg | 3900 |
| cacaggcgca tggccacatg aagcccctga cggcatccca ggtcagtgtg cataggca | 3960 |
| tggatgacag gtggcgggac tccccagggg ccacaccatg ggaccaggtc agctatgtca | 4020 |
| gccaggtgtc gctgtcctcc ctgacgtccg acaagccatc tcggcacagc gctgcagcag | 4080 |
| acgatgatgg ggacaagtgg tctctgctcc tgaatggcag ggatgaggag cagtacatct | 4140 |
| gagatccaga catgataaga tacattgatg agtttggaca aaccacaact agaatgcagt | 4200 |
| gaaaaaatg ctttatttgt gaaatttgtg atgctattgc tttatttgta accattataa | 4260 |
| gctgcaataa acaagttaac aacaacaatt gcattcattt tatgtttcag gttcaggggg | 4320 |
| aggtgtggga ggttttttag aggaacccct agtgatggag ttggccactc cctctctgcg | 4380 |
| cgctcgctcg ctcactgagg ccgcccgggc aaagcccggg cgtcgggcga cctttggtcg | 4440 |
| cccggcctca gtgagcgagc gagcgcgcag agagggagtg gccaa | 4485 |

<210> SEQ ID NO 15
<211> LENGTH: 3603
<212> TYPE: DNA
<213> ORGANISM: Artificial Sequence
<220> FEATURE:
<223> OTHER INFORMATION: Description of artificial sequence: Del 1-3
    ATP7B, codon-optimized

<400> SEQUENCE: 15

| | |
|---|---|
| atgcccgagc aggaaagaca gatcaccgcc agagagggcg ccagccggaa gatcctgagc | 60 |
| aagctgagcc tgcccaccag agcctgggag cccgccatga agaagtcctt cgccttcgac | 120 |
| aacgtgggct acgagggcgg cctggacgga ctgggaccat cttctcaggt ggccacaagc | 180 |
| accgtgcgcg acgagccga gggctccgga acagatcaca gaagcagcag cagccacagc | 240 |
| cctggcagcc ccctagaaa tcaggtgcag ggcacctgta gcaccaccct gatcgccatt | 300 |

```
gccggcatga catgcgccag ctgcgtgcac tctattgagg gcatgatctc ccagctggaa      360
ggcgtgcagc agatcagtgt gtctctggcc gagggcaccg ccacagtgct gtacaaccct      420
agcgtgatca gccccgaaga actgagagcc gccattgagg acatgggatt cgaagccagc      480
gtggtgtccg agagctgctc caccaaccct ctgggcaatc acagcgccgg caacagcatg      540
gtgcagacca ccgacggcac ccccaccagc gtgcaggaag tggccccaca tacaggcaga      600
ctgcccgcca atcacgcccc cgatatcctg gccaagagcc cccagagtac aagagccgtg      660 gcccccccaga agtgcttcct gcagatcaag ggcatgactt gtgcctcttg tgtgtccaat      720
atcgagcgga acctgcagaa agaggccggc gtgctgtctg tgctggtggc tctgatggcc      780
ggcaaggccg agatcaaata cgaccccgaa gtgattcagc ccctggaaat cgcccagttt      840
atccaggacc tgggctttga agccgccgtg atggaagatt acgccggctc cgacggcaac      900
atcgagctga ccatcaccgg aatgacctgc gcctcctgtg tgcacaacat tgagtccaag      960
ctgacccgga ccaacggcat cacctacgcc tctgtggctc tggccaccte caaggccctc     1020 gtgaagttcg atcccgagat catcggcccc aggacatca tcaagatcat cgaagagatc     1080
ggcttccacg ccagcctggc ccagaggaac cctaacgccc accacctgga ccacaagatg     1140
gaaatcaagc agtggaagaa aagcttcctg tgcagcctgg tgttcggcat ccccgtgatg     1200
gccctgatga tctacatgct gatccccagc aacgagcccc accagtccat ggtgctggat     1260
cacaacatca tccccggcct gtctatcctg aacctgatct tcttcatcct gtgcaccttc     1320
gtgcagctgc tgggcggctg gtacttctac gtgcaggcct acaagtccct gcggcacaga     1380
tccgccaaca tggacgtgct gatcgtgctg gccacatcta tcgcctacgt gtactccctc     1440
gtgatcctgg tggtggccgt ggccgagaaa gccgagagaa gccctgtgac cttcttcgac     1500 accccccta tgctgttcgt gtttatcgcc ctgggccggt ggctggaaca cctggccaaa     1560
agcaagacca gcgaggccct ggctaagctg atgagtctgc aggccaccga ggccacagtc     1620
gtgaccctgg gcgaggacaa cctgatcatc cgcgaggaac aggtgccaat ggaactggtg     1680
cagcggggcg acatcgtgaa ggtggtgcct ggcggcaagt tccccgtgga cggaaaagtg     1740
ctggaaggga ataccatggc cgacgagagc ctgatcacag cgaggccat gcccgtgacc     1800 aagaaacctg gcagcacagt gatcgccggc agcatcaatg cccacggcag cgtgctgatt     1860
aaggccacac acgtgggcaa cgataccacc ctggctcaga ttgtgaagct ggtggaagag     1920
gcccagatga gcaaggcccc cattcagcag ctggctgacc ggttcagcgg ctacttcgtg     1980 cccttatca tcatcatgag caccctgaca ctggtcgtgt ggatcgtgat cggctttatc     2040
gacttcggag tggtgcagag atacttcccc aaccctaaca agcacatcag ccagacagaa     2100
gtgatcatca gattcgcctt tcagaccagc atcaccgtgc tgtgtatcgc ctgccccctgt     2160 agcctgggac tggccacacc taccgctgtg atggtgggaa caggcgtggc cgctcagaac     2220
ggcatcctga tcaaggggg caagcctctg gaaatggctc acaagatcaa gaccgtgatg     2280
ttcgacaaga ccggcaccat cacccacggc gtgcccagag tgatgagagt gctgctgctg     2340
ggggatgtgg ccaccctgcc tctgagaaag gtgctggctg tcgtgggcac agccgaggct     2400
agctctgaac acccactggg agtggccgtg acaaagtact gcaaagagga actgggcacc     2460
gaaaccctgg ctactgcac cgactttcag gccgtgcctg gctgtggcat cggctgcaag     2520
gtgtccaacg tggaaggcat cctggcccac agcgagaggc cactgtctgc ccctgccagc     2580
cacctgaacg aggccggatc tctgcccgcc gaaaaggacg ctgtgcccca gaccttctct     2640
```

```
gtgctgattg gcaacagaga gtggctgcgg cggaacggcc tgaccatctc ctccgatgtg    2700
tccgacgcca tgaccgacca cgagatgaag ggccagaccg ccattctggt ggccattgac    2760
ggggtgctgt gcggcatgat cgcaatcgcc gatgccgtga acaggaagc agcactggcc     2820 gtgcacaccc tgcagtctat gggagtggat gtggtgctga tcaccggcga caacagaaag    2880
accgccaggg ccattgccac ccaggtgggc atcaacaagg tgttcgccga ggtgctgccc    2940
agccacaaag tggccaaggt gcaggaactg cagaacaaag gcaaaaaggt ggccatggtg    3000
ggagatggcg tgaacgactc tcctgctctg gcccaggcag atatgggcgt ggccatcggc    3060
acaggcaccg acgtggcaat tgaggctgct gacgtggtgc tgattcggaa cgacctgctg    3120
gacgtggtgg cctccatcca cctgtccaag agaaccgtgc ggcggatcag aatcaacctg    3180
gtgctggcac tgatctataa cctcgtgggc atccctatcg ccgctggcgt gttcatgcct    3240
atcggaatcg tgctgcagcc ctggatgggc tctgccgcca tggctgcaag ctccgtgtct    3300
gtggtgctgt ccagcctgca gctgaagtgc tacaagaagc ccgacctgga aagatacgag    3360
gcccaggccc acgacacat gaagcctctg acagcctccc aggtgtccgt gcacatcggc     3420
atggacgaca gatggcggga cagccctaga gccaccccctt gggatcaggt gtcatacgtg    3480
tcacaggtgt ccctgagcag cctgaccagc gacaagccca gcagacatag cgccgctgcc    3540
gacgacgatg gggacaagtg gtccctgctg ctgaacggcc gggatgagga acagtacatc    3600
tga                                                                  3603
```

GENE THERAPY CONSTRUCTS FOR TREATING WILSON DISEASE

CROSS-REFERENCE TO RELATED APPLICATIONS

This application is a U.S. national stage application, filed under 35 U.S.C. § 371, of International Application No. PCT/US2020/012131, filed on Jan. 3, 2020, which claims the benefit of and priority to U.S. Provisional Patent Application No. 62/788,324, filed on Jan. 4, 2019; and to U.S. Provisional Patent Application No. 62/834,830, filed on Apr. 16, 2019, the entire disclosure of each of which are incorporated herein by reference for all purposes.

SEQUENCE LISTING

The instant application contains a Sequence Listing which has been submitted electronically in ASCII format and is hereby incorporated by reference in its entirety. Said ASCII copy, created on Dec. 31, 2019, is named ULP-003WO_SL_ST25.txt and is 49,846 bytes in size.

TECHNICAL FIELD OF THE INVENTION

This application relates generally to adeno-associated viral vectors and methods of their use in gene therapy for treating Wilson disease (WD).

BACKGROUND OF THE INVENTION

Wilson disease (WD) is an autosomal recessive genetic disorder that causes accumulation of copper primarily in the liver and subsequently in the neurological system and other tissues. WD is a rare disorder that affects approximately 1 in 30,000 individuals, caused by mutations in the copper transporting ATPase 2 (ATP7B) gene on chromosome 13. There are more than 600 unique ATP7B mutations. ATP7B is expressed mainly in hepatocytes and functions in the transmembrane transport of copper. Absent or reduced function of ATP7B protein results in decreased hepatocellular excretion of copper into bile, causing liver disease. Over time without proper treatment, high copper levels can cause life-threatening organ damage.

Patients with hepatic WD usually present in late childhood or adolescence, and exhibit features of acute hepatitis, fulminant hepatic failure, or progressive chronic liver disease. Neurologic manifestations of WD typically present later than the liver disease, most often in the second or third decade and include extrapyramidal, cerebellar, and cerebral-related symptoms.

The aim of medical treatment of WD is to remove the toxic deposit of copper from the body and to prevent its reaccumulation. Current treatment approaches for WD are daily oral therapy with chelating agents (D-penicillamine, trientine, and zinc salts). Medical therapy is effective in most, but not all WD patients. Liver transplantation is a therapeutic option in WD patients presenting with fulminant liver failure or progressive liver failure. However, transplant recipients are required to maintain a constant immune suppression regimen to prevent rejection.

The present invention addresses the need for improved and sustainable treatment of WD by delivering a gene expressing truncated yet functional ATP7B to patients with an adeno-associated viral vector. The truncated ATP7B of the present invention has improved efficacy in treating WD and possesses an advantage of manufacturing ease and efficiency over wild-type and other truncated forms of ATP7B protein.

SUMMARY OF THE INVENTION

This invention provides compositions and methods of their use in gene therapy. Provided herein are adeno-associated virus (AAV) vectors useful for the treatment of WD. In one aspect, the present invention provides a recombinant nucleic acid construct comprising: a 5'-inverted terminal repeat (ITR) sequence; a promoter sequence; a nucleic acid sequence encoding a truncated human copper-transporting ATPase 2 (ATP7B) in which metal-binding domains (MBDs) 1-3 have been deleted, but the serine-rich loop including two serine residues (S340 and S341) between MBD3 and MBD4 is present; and a 3'-ITR sequence.

In another aspect, the present invention provides a recombinant adeno-associated virus (rAAV) useful for the treatment of Wilson disease, in which rAAV comprises an AAV capsid and a vector genome packaged therein, the vector genome comprises a 5'-inverted terminal repeat (ITR) sequence; a promoter sequence; a nucleic acid sequence encoding a truncated human copper-transporting ATPase 2 (ATP7B) in which metal-binding domains (MBDs) 1-3 have been deleted, but the serine-rich loop including two serine residues (S340 and S341) between MBD3 and MBD4 is present; and a 3'-ITR sequence.

These and other aspects and features of the invention are described in the following sections of the application.

BRIEF DESCRIPTION OF THE DRAWINGS

The invention can be more completely understood with reference to the following drawings.

| Start (Nucleotide Position) | End (Nucleotide Position) | Description |
|---|---|---|
| 1 | 145 | Inverted terminal repeat (ITR) |
| 146 | 245 | Enhancer |
| 246 | 435 | Promoter |
| 436 | 530 | Intron |
| 531 | 536 | Consensus Kozak sequence |
| 540 | 4142 | ATP7B dell-3 native (wild-type) cDNA |
| 4143 | 4340 | Poly A signal |
| 4341 | 4485 | Inverted terminal repeat (ITR) |

Figure 2:
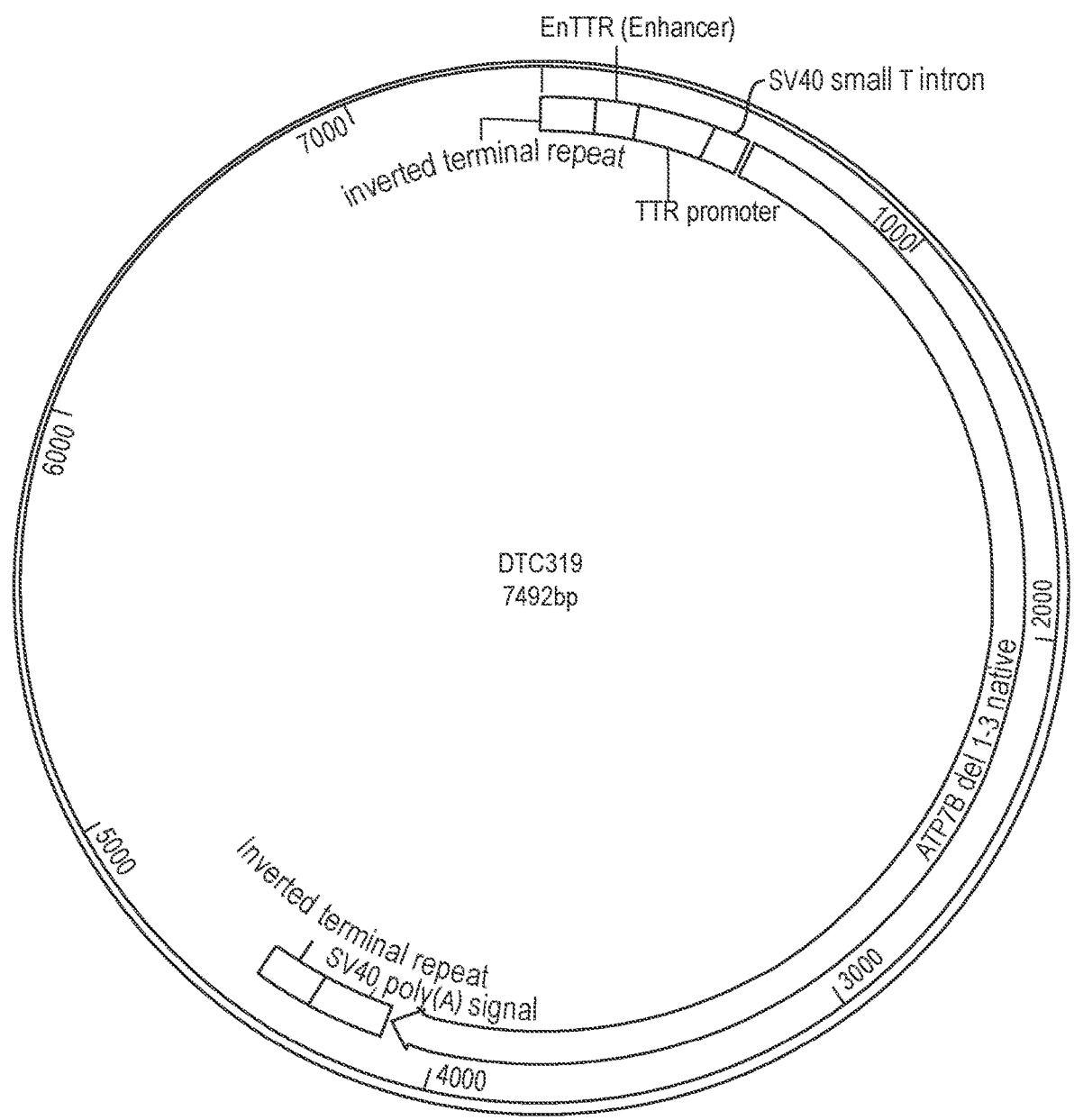

FIG. 2 is a schematic representation of an exemplary AAV vector (DTC319), with various key components shown therein.

Figure 3:
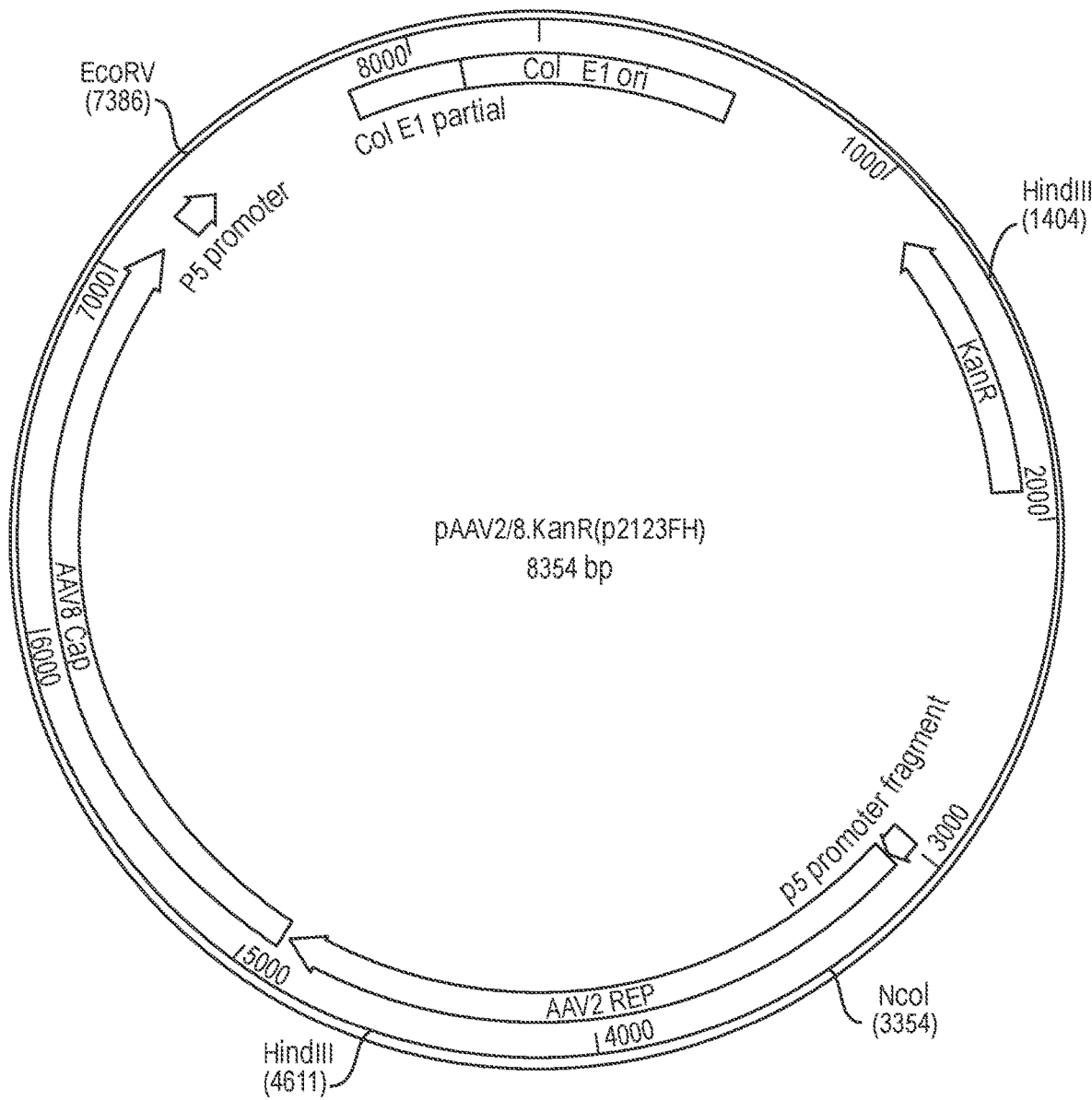

FIG. 3 is a schematic representation of an exemplary plasmid, pAAV2/8.KanR (p2123FH) AAV Rep/Cap plasmid, which provides Rep and Cap function in packaging rAAV when co-transfected with AAV vectors into host cells.

Figure 4:
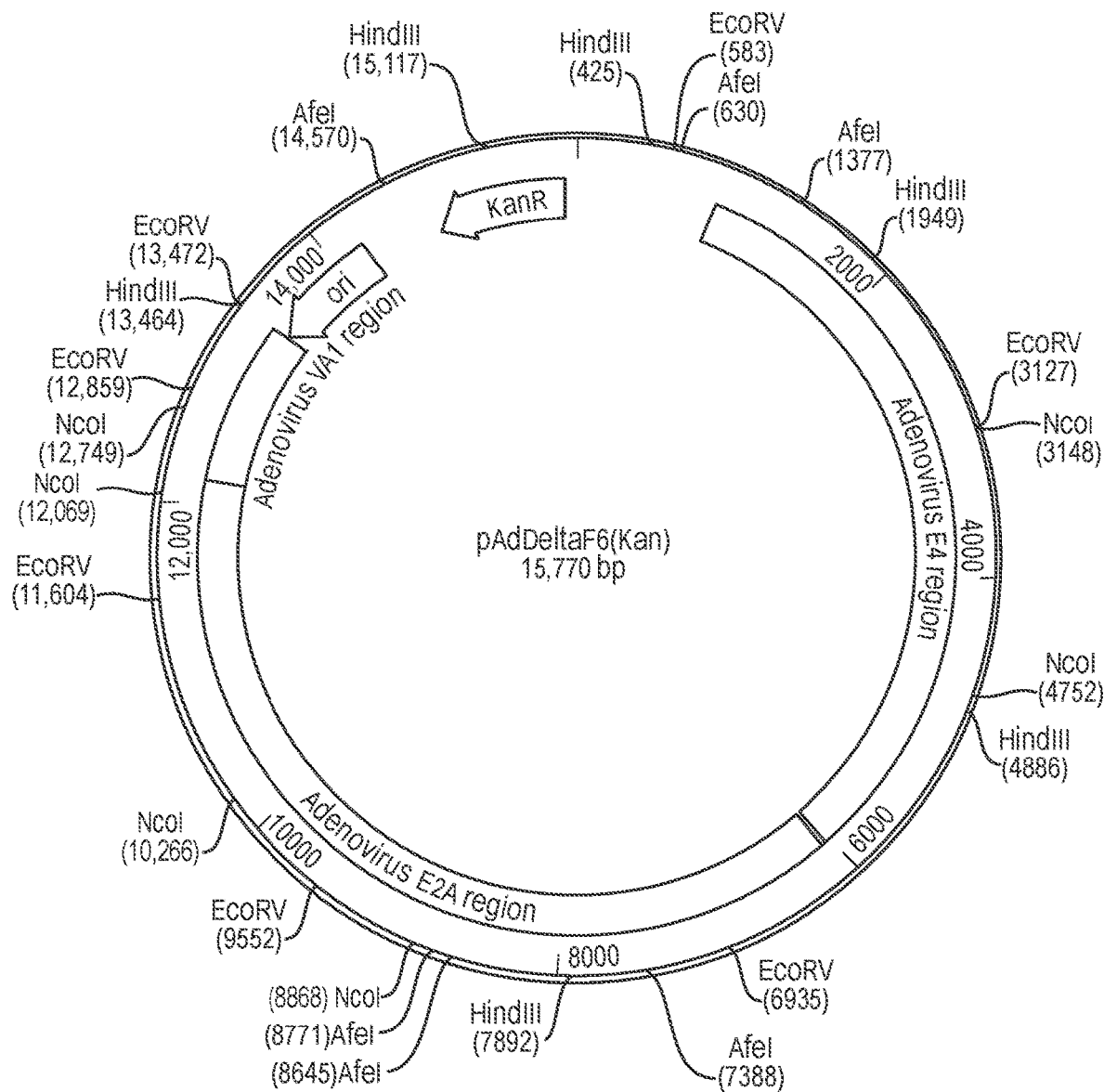

FIG. 4 is a schematic representation of an exemplary plasmid, pAdDeltaF6 (Kan) adenovirus helper plasmid, for rAAV production when co-transfected with AAV vectors and Rep/Cap plasmids into host cells.

Figure 5:
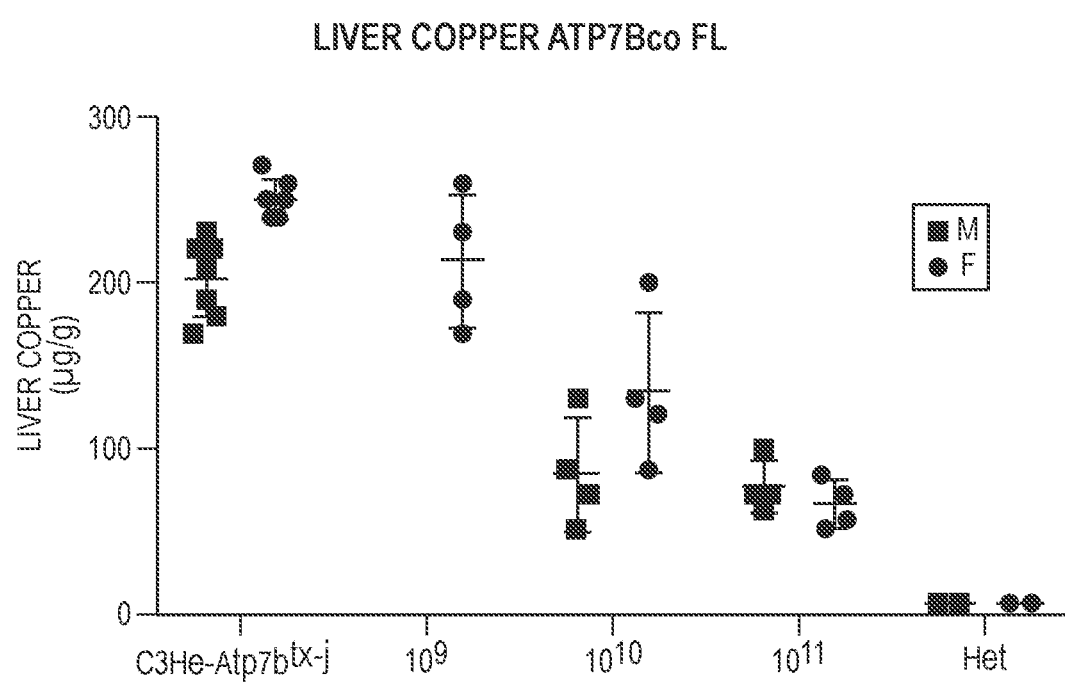

FIG. 5 is a scatter plot of liver copper (μg/g) in C3He-Atp7b$^{tx-j}$ female mice (represented by circles) injected with either $10^9$, $10^{10}$, or $10^{11}$ genome copies (GC)/kg of ATP7BcoFL (full-length human ATP7B which has been codon-optimized) and C3He-Atp7b$^{tx-j}$ male mice (represented by squares) injected with either $10^{10}$ or $10^{11}$ GC/kg of the same vector. Copper levels from age-matched uninjected male and female heterozygous (Het) and C3He-Atp7b$^{tx-j}$ mice are also represented in the scatter plot.

Figure 6:
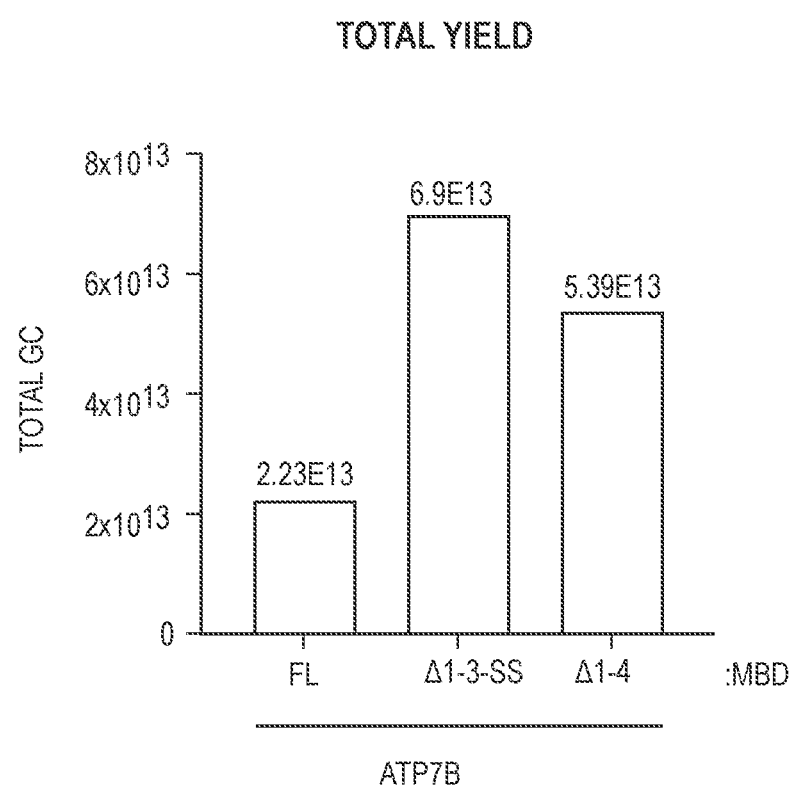

FIG. 6 is a bar graph showing total yield rAAV (titers in GC) produced from host cells after transfection of AAV vectors encoding full or partial coding sequences of human ATP7B (AAV vector carrying nucleotide sequence for encoding full-length (FL) human ATP7B; AAV vector carrying nucleotide sequence for encoding human ATP7B in which MBDs 1-3 have been deleted, but the serine-rich loop including two serine residues (S340 and S341) between MBD3 and MBD4 is present (ATP7B Δ1-3-SS); or AAV vector carrying nucleotide sequence for encoding human ATP7B in which MBDs 1-4 have been deleted (ATP7B Δ1-4).

Figure 7:
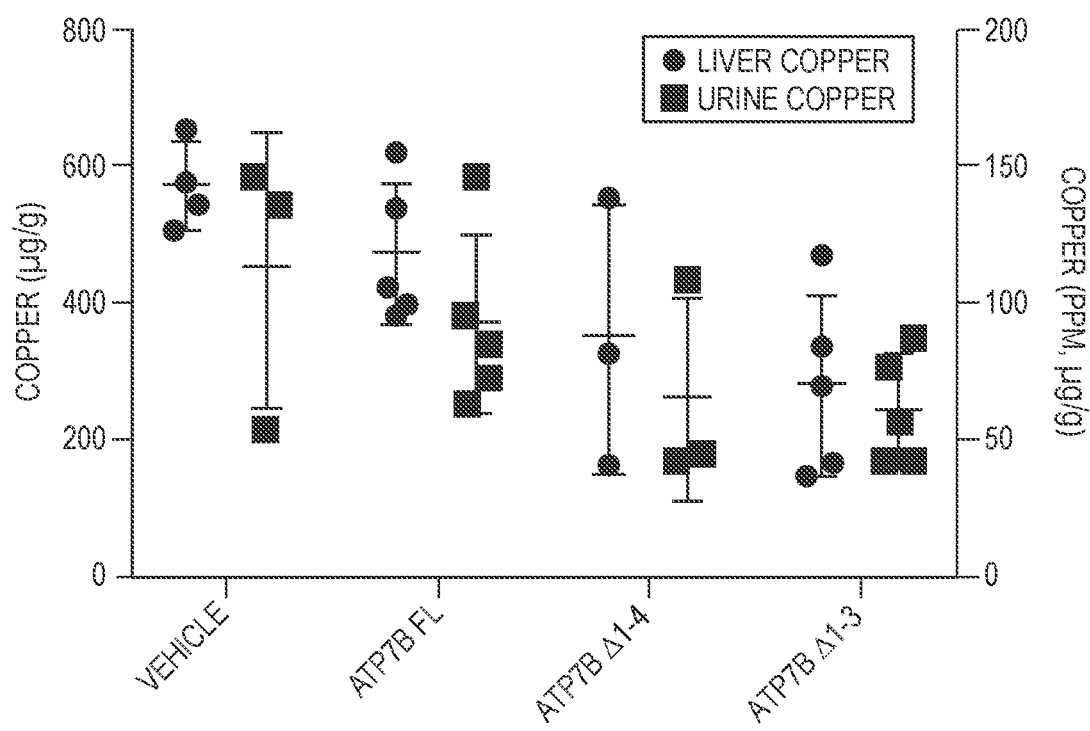

FIG. 7 is a scatter plot of urine and liver copper levels, squares and circles, respectively (μg/g), assayed after C3He-Atp7b$^{tx-j}$ mice were injected with AAV8 carrying full-length human ATP7B (ATP7B FL), ATP7B Δ1-3-SS, or ATP7B Δ1-4. Phosphate-buffered saline (PBS) administered C3He-Atp7b$^{tx-j}$ mice served as controls (vehicle).

Figure 8:
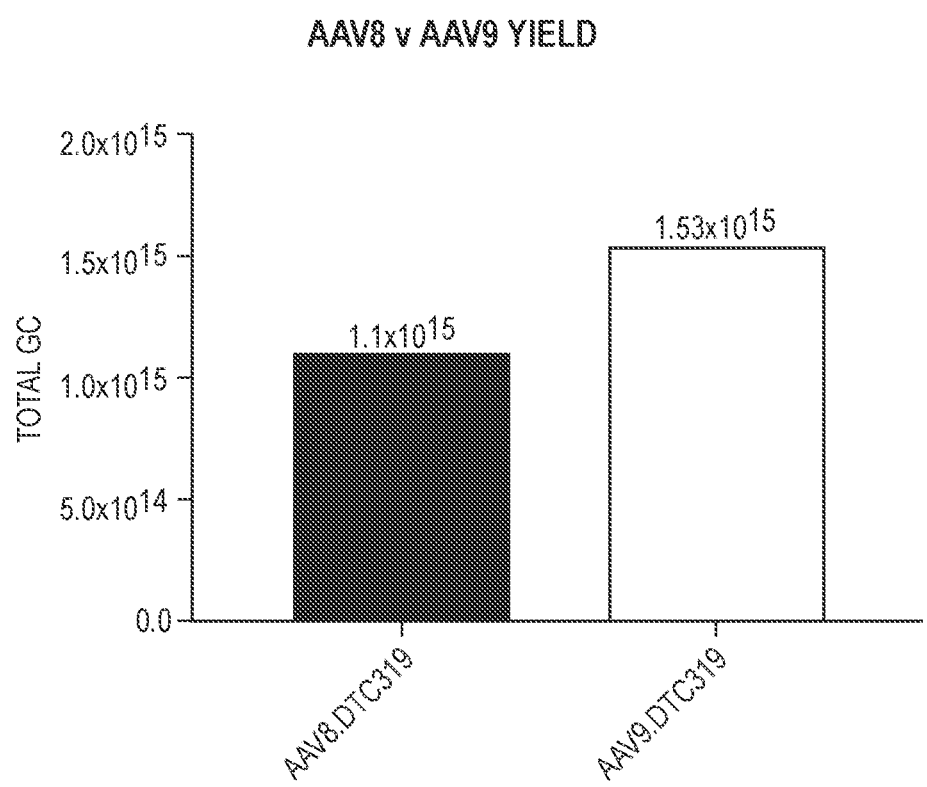

FIG. 8 is a bar graph showing total yield rAAV (titers in GC) produced from host cells after transfection of AAV vector (DTC319) that encodes a truncated human ATP7B, in which metal-binding domains (MBDs) 1-3 have been deleted, but the serine-rich loop including two serine residues (S340 and S341) between MBD3 and MBD4 is present, encoding either AAV8 or AAV9 capsid.

Figure 9:
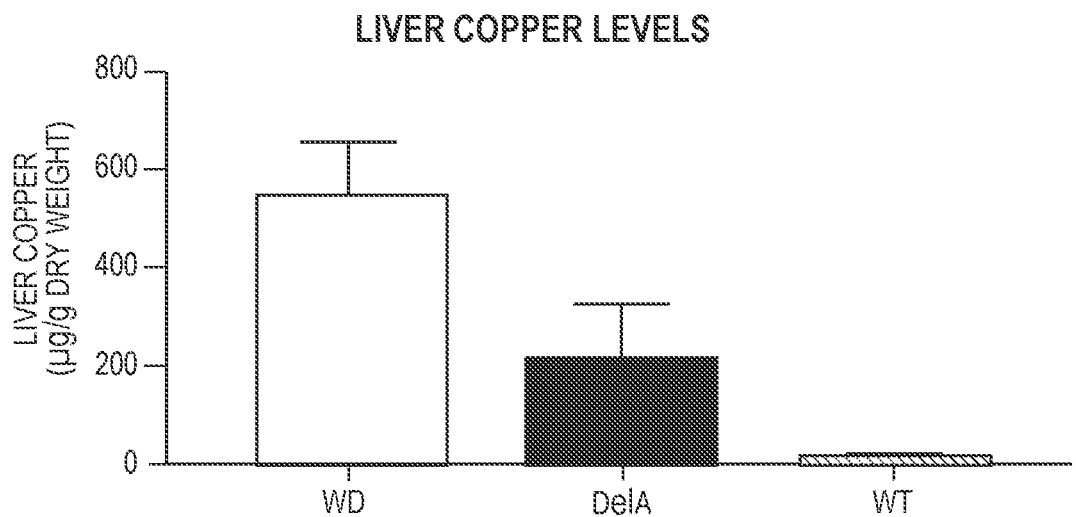

FIG. 9 is a bar graph of liver copper accumulation levels (μg/g dry weight) in C3He-Atp7b$^{tx-j}$ mice that were administered an intravenous injection of a vehicle control (dilution buffer; WD) or an infusion of AAV8 carrying native ATP7B Δ1-3-SS (DelA). Liver copper accumulation levels in uninjected wild-type mice (WT) represented in the bar graph served as a negative control. Values expressed as mean±SEM (standard error of the mean).

Figure 10:
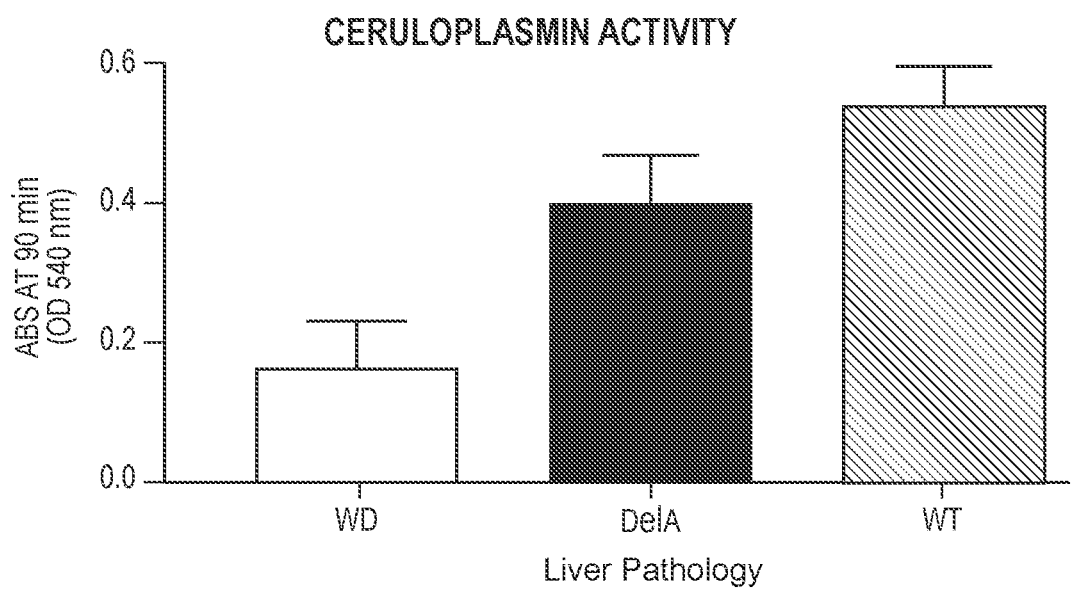

FIG. 10 is a bar graph of ceruloplasmin activity in C3He-Atp7b$^{tx-j}$ mice that were administered an intravenous injection of a vehicle control (dilution buffer; WD) or an infusion of AAV8 carrying native ATP7B Δ1-3-SS (DelA), as measured by an enzymatic reaction-based colorimetric activity assay. Ceruloplasmin activity in uninjected wild-type (WT) mice, as measured by the same enzymatic reaction-based colorimetric activity assay is also represented in the bar graph.

Figure 11:
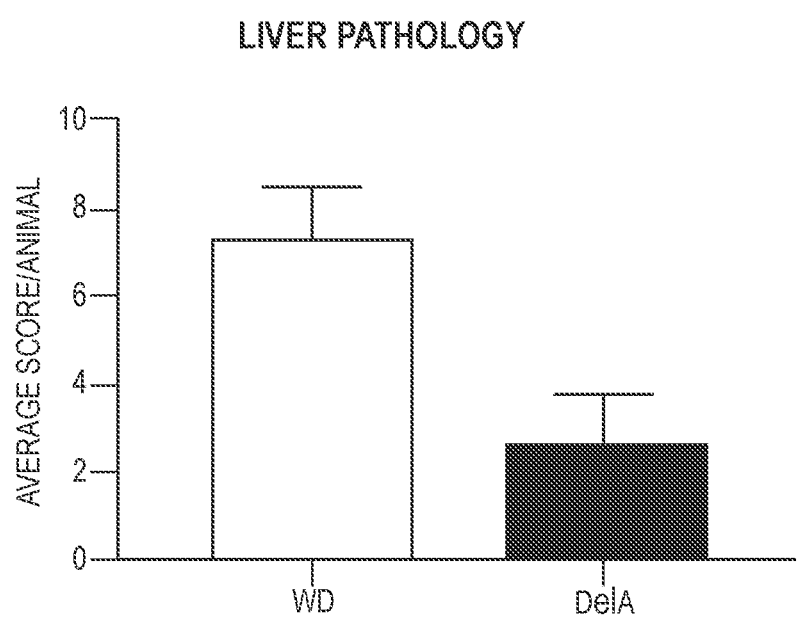

FIG. 11 is a bar graph of the average score after standard assessment of Hematoxylin and Eosin (H&E) slides for nuclear enlargement and hepatocellular hypertrophy, disorganization, inflammatory infiltrate, and hepatocellular necrosis.

Figure 12:
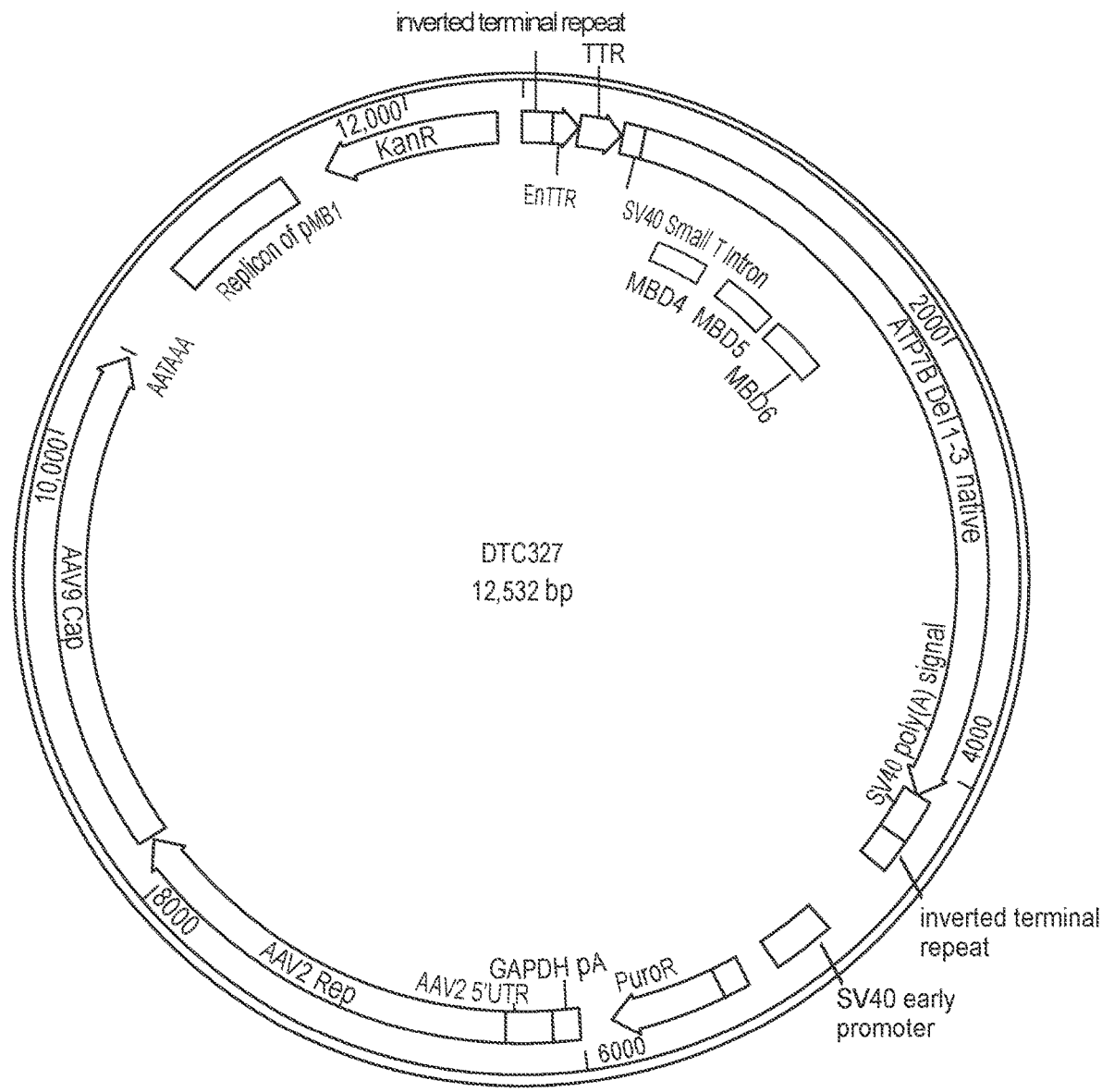

FIG. 12 is an illustrative diagram showing an exemplary vector genome construct DTC327 comprising an AAV9 capsid with PPIA polyA, AAV2 Rep/ITRs with full p5 promoter comprising 145 bps ITRs, and a nucleotide sequence encoding a truncated human copper-transporting ATPase 2 (ATP7B), in which the metal-binding domains (MBDs) 1-3 have been deleted, but the serine-rich loop including two serine residues (S340 and S341) between MBD3 and MBD4 is present.

DETAILED DESCRIPTION OF THE INVENTION

This invention provides agents and compositions for use in treating Wilson disease (WD). The nucleic acid sequences, vectors, recombinant viruses, and associated compositions of this invention as described herein can be used for ameliorating, preventing, or treating WD.

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adeno-associated virus (AAV): A small, replication-defective, non-enveloped virus that infects humans and some other primate species. AAV is not known to cause disease and elicits a very mild immune response. Gene therapy vectors that utilize AAV can infect both dividing and quiescent cells and can persist in an extrachromosomal state without integrating into the genome of the host cell. These features make AAV an attractive viral vector for gene therapy. There are currently 12 recognized serotypes of AAV (AAV1-12).

Administration/Administer: To provide or give a subject an agent, such as a therapeutic agent (e.g., a recombinant AAV), by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal, and inhalation routes.

ATP7B Δ1-3-SS: As used herein, ATP7B Δ1-3-SS refers to a truncated human copper-transporting ATPase 2 (ATP7B), in which the metal-binding domains (MBDs) 1-3 have been deleted, but the serine-rich loop including two serine residues (S340 and S341) between MBD3 and MBD4 is present.

Codon-optimized: A "codon-optimized" nucleic acid refers to a nucleic acid sequence that has been altered such that the codons are optimal for expression in a particular system (such as a particular species or group of species). For example, a nucleic acid sequence can be optimized for expression in mammalian cells or in a particular mammalian species (such as human cells). Codon optimization does not alter the amino acid sequence of the encoded protein.

Enhancer: A nucleic acid sequence that increases the rate of transcription by increasing the activity of a promoter.

Intron: A stretch of DNA within a gene that does not contain coding information for a protein. Introns are removed before translation of a messenger RNA.

Inverted terminal repeat (ITR): Symmetrical nucleic acid sequences in the genome of adeno-associated viruses required for efficient replication. ITR sequences are located at each end of the AAV DNA genome. The ITRs serve as the origins of replication for viral DNA synthesis and are required for vector encapsidation.

Isolated: An "isolated" biological component (such as a nucleic acid molecule, protein, virus or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease (such as WD) refers to inhibiting the full development of a disease. "Treating" refers to a therapeutic intervention that ameliorates a sign or symptom of a disease or pathological condition (such as WD) after it has begun to develop. "Ameliorating" refers to the reduction in the number or severity of signs or symptoms of a disease (such as WD).

Promoter: A region of DNA that directs/initiates transcription of a nucleic acid (e.g., a gene). A promoter includes necessary nucleic acid sequences near the start site of transcription.

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques.

Similarly, a recombinant virus is a virus comprising sequence (such as genomic sequence) that is non-naturally occurring or made by artificial combination of at least two sequences of different origin. The term "recombinant" also includes nucleic acids, proteins and viruses that have been altered solely by addition, substitution, or deletion of a portion of a natural nucleic acid molecule, protein or virus. As used herein, "recombinant AAV" refers to an AAV particle in which a recombinant nucleic acid molecule such as a recombinant nucleic acid molecule encoding a truncated human ATP7B (e.g., SEQ ID NO:1 or SEQ ID NO:15) has been packaged.

Sequence identity: The identity or similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970: Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992: and Pearson et al., *Meth. Mol. Rio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI) and on the internet, for use in connection with the sequence analysis programs blastp, blastn, blastx, tblastn and tblastx. Additional information can be found at the NCBI web site.

Serotype: A group of closely related microorganisms (such as viruses) distinguished by a characteristic set of antigens.

Stuffer sequence: Refers to a sequence of nucleotides contained within a larger nucleic acid molecule (such as a vector) that is typically used to create desired spacing between two nucleic acid features (such as between a promoter and a coding sequence), or to extend a nucleic acid molecule so that it is of a desired length. Stuffer sequences do not contain protein coding information and can be of unknown/synthetic origin and/or unrelated to other nucleic acid sequences within a larger nucleic acid molecule.

Subject: Living multi-cellular vertebrate organisms, a category that includes human and non-human mammals.

Synthetic: Produced by artificial means in a laboratory, for example a synthetic nucleic acid can be chemically synthesized in a laboratory.

Therapeutically effective amount: A quantity of a specified pharmaceutical or therapeutic agent (e.g., a recombinant AAV) sufficient to achieve a desired effect in a subject, or in a cell, being treated with the agent. The effective amount of the agent will be dependent on several factors, including, but not limited to the subject or cells being treated, and the manner of administration of the therapeutic composition.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes. In some embodiments herein, the vector is an AAV vector.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Viral Vectors:

In some aspects, the present disclosure provides a recombinant adeno-associated virus (AAV) vector containing a genome comprising an AAV 5'-inverted terminal repeat (ITR) sequence, a promoter sequence, a nucleic acid sequence which encodes ATP7B Δ1-3-SS (e.g., SEQ ID NO:1 or SEQ ID NO:15), and an AAV 3'-inverted terminal repeat sequence (ITR).

In some embodiments, the genome may further comprise an enhancer, an intron, a consensus Kozak sequence, and/or a polyadenylation signal as described herein. In some embodiments, the recombinant vector can further include one or more stuffer nucleic acid sequences. In one embodiment, a stuffer nucleic acid sequence is situated between the intron and the partial or complete coding sequence for ATP7B.

In various embodiments described herein, the recombinant virus vector is an adeno-associated virus (AAV) vector. The AAV vector can be an AAV vector of serotype 1, 2, 3, 4, 5, 6, 7, 8, 9, 10, 11, or 12 (i.e., AAV1, AAV2, AAV3, AAV4, AAV5, AAV6, AAV7, AAV8, AAV9, AAV10, AAV11, or AAV12), as well as any one of the more than 100 variants isolated from human and nonhuman primate tissues. See, e.g., Choi et al., 2005, *Curr Gene Ther.* 5: 299-310, 2005 and Gao et al., 2005, *Curr Gene Ther.* 5: 285-297. AAV vectors of any serotype may be used in the present invention, and the selection of AAV serotype will depend in part on the cell type(s) that are targeted for gene therapy. For treatment of WD, the liver is one of the relevant target organs. In some embodiments, the AAV vector is selected from serotype 9 (AAV9), serotype 8 (AAV8), serotype 5 (AAV5), or variant thereof. In an exemplary embodiment, the AAV vector is serotype 9 (AAV9) or a variant thereof.

In some embodiments, the recombinant AAV vector includes an AAV ITR sequence, which functions as both the origin of vector DNA replication and the packaging signal of the vector genome, when AAV and adenovirus helper functions are provided in trans. Additionally, the ITRs serve as the target for single-stranded endonucleatic nicking by the large Rep proteins, resolving individual genomes from replication intermediates.

In some embodiments, the 5'-ITR sequence is from AAV2. In some embodiments, the 3'-ITR sequence is from AAV2. In some embodiments, the 5'-ITR sequence and the 3'-ITR sequence are from AAV2. In some embodiments, the 5'-ITR sequence and/or the 3'-ITR sequence are from AAV2 and comprise or consist of SEQ ID NO:2. In other embodiments, the 5'-ITR sequence and/or the 3'-ITR sequence are from a non-AAV2 source.

In some exemplary embodiments, the AAV vector is an AAV serotype 9 (AAV9) vector, and the vector includes an enhancer, a promoter, an intron, a nucleic acid sequence which encodes ATP7B Δ1-3-SS (e.g., SEQ ID NO:1 or SEQ ID NO:15), and a polyadenylation signal described herein. In some embodiments, the AAV9 vector further includes two AAV2, AAV8, or AAV9 inverted terminal repeat (ITR) sequences: one 5' of the enhancer and another 3' of the polyadenylation signal. In an exemplary embodiment, the AAV9 vector includes two AAV2 inverted terminal repeat (ITR) sequences: one 5' of the enhancer and another 3' of the polyadenylation signal. In some embodiments, the AAV2 ITR sequences comprise or consist of SEQ ID NO:2. In another exemplary embodiment, the AAV9 vector includes two AAV9 inverted terminal repeat (ITR) sequences: one 5' of the enhancer and another 3' of the polyadenylation signal.

In some exemplary embodiments, the present disclosure provides a recombinant nucleic acid comprising a vector genome comprising an AAV 5'-inverted terminal repeat (ITR) sequence, a promoter sequence, a nucleic acid sequence represented by SEQ ID NO:1, which encodes native ATP7B Δ1-3-SS, and an AAV 3'-inverted terminal repeat sequence (ITR). In some exemplary embodiments, the present disclosure provides a recombinant nucleic acid comprising a vector genome comprising an AAV 5'-inverted terminal repeat (ITR) sequence, a promoter sequence, a nucleic acid sequence represented by SEQ ID NO:15, which encodes a codon-optimized ATP7B Δ1-3-SS, and an AAV 3'-inverted terminal repeat sequence (ITR). In some exemplary embodiments, the present disclosure provides a vector genome comprising of SEQ ID NO:14, which comprises an AAV 5'-inverted terminal repeat (ITR) sequence, a promoter sequence, a nucleic acid sequence represented by SEQ ID NO:1, which encodes native ATP7B Δ1-3-SS, or an adeno-associated virus (AAV) vector comprising the same.

In additional aspects, the application provides recombinant nucleic acid sequences corresponding to vector genomes useful in the treatment of WD. In some embodiments, the application provides a recombinant nucleic acid which is 80%, 85%, 90%, 91%, 92%, 93%, 94%, 95%, 96%, 97%, 98%, 99% or more identical to SEQ ID NO:14. Thus, the application provides recombinant nucleic acids which are at least 80% (e.g., 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100%) identical to SEQ ID NO:14. In an exemplary embodiment, the application provides a recombinant nucleic acid sequence corresponding to a vector genome comprising an AAV 5'-inverted terminal repeat (ITR) sequence, a promoter sequence, a nucleic acid sequence represented by SEQ ID NO:1, which encodes native ATP7B Δ1-3-SS, and an AAV 3'-inverted terminal repeat sequence (ITR), wherein the vector genome comprises or consists of SEQ ID NO:14. In an exemplary embodiment, the application provides a recombinant nucleic acid sequence corresponding to a vector genome comprising an AAV 5'-inverted terminal repeat (ITR) sequence, a promoter sequence, a nucleic acid sequence represented by SEQ ID NO:15, which encodes a codon-optimized ATP7B Δ1-3-SS, and an AAV 3'-inverted terminal repeat sequence (ITR).

Promoter:

In various aspects described herein, AAV vectors are provided which comprises a promoter sequence which helps drive and regulate transgene expression, e.g., expression of ATP7B Δ1-3-SS (e.g., amino acid sequence of ATP7B Δ1-3-SS represented by SEQ ID NO:8). In exemplary embodiments, the promoter sequence is located between the selected 5'-ITR sequence and the coding sequence for ATP7B Δ1-3-SS (e.g., SEQ ID NO:1 or SEQ ID NO:15). In some embodiments, the promoter sequence is located downstream of an enhancer sequence. In some embodiments the promoter sequence is located upstream of an intron sequence. In some illustrative embodiments, a vector described herein uses the transthyretin (TTR) promoter, which may optionally be located downstream of a transthyretin enhancer (enTTR).

In some embodiments, the promoter is selected from a transthyretin (TTR) promoter, a chicken β-actin (CBA) promoter, a cytomegalovirus immediate early gene (CMV) promoter, a thyroxine binding globulin (TBG) promoter, an alpha-1 anti-trypsin (A1AT) promoter, and a CAG promoter (constructed using the CMV early enhancer element, the promoter, the first exon, and the first intron of CBA gene, and the splice acceptor of the rabbit beta-globin gene). In an exemplary embodiment, the promoter is the TTR promoter. In one embodiment, the TTR promoter comprises or consists of SEQ ID NO:12.

In addition to a promoter, an AAV vector may contain other appropriate transcription initiation, termination, enhancer sequence, and efficient RNA processing signals. As described in further detail below, such sequences include splicing and polyadenylation (poly A) signals, regulatory elements that enhance expression (i.e., WPRE), sequences that stabilize cytoplasmic mRNA, sequences that enhance translation efficiency (i.e., the Kozak consensus sequence), and sequences that enhance protein stability.

In some embodiments, the AAV vector contains a vector genome that further comprises a consensus Kozak sequence. In some embodiments, the consensus Kozak sequence is located downstream of an intron sequence. In one embodiment, the consensus Kozak sequence is GCCGCC (SEQ ID NO:11). As will be understood by those skilled in the art, the consensus Kozak sequence is typically located immediately upstream of a coding sequence; in this case, immediately upstream of a coding sequence for truncated ATP7B (ATP7B Δ1-3-SS) (e.g., SEQ ID NO:1 or SEQ ID NO:15). As will be appreciated by the skilled artisan, the consensus Kozak sequence can be considered to share an ATG residue corresponding to the start codon of the therapeutic polypeptide, e.g., truncated ATP7B (ATP7B Δ1-3-SS) (e.g., SEQ ID NO:1 or SEQ ID NO:15). For the simplicity of disclosure, the consensus Kozak sequence, as described herein, comprises a six-nucleotide sequence corresponding to the region not shared with the nucleic acid encoding the therapeutic polypeptide, e.g., truncated ATP7B (ATP7B Δ1-3-SS encoded by SEQ ID NO:1 or SEQ ID NO:15).

ATP7B Polypeptides:

As described herein, aspects of the invention provide recombinant vectors that include a genome that comprises an AAV 5'-inverted terminal repeat sequence (ITR), a promoter sequence, a coding sequence for truncated human ATP7B (ATP7B Δ1-3-SS) having an amino acid sequence of SEQ ID NO:8 (e.g., SEQ ID NO:1 or SEQ ID NO:15), and an AAV 3'-inverted terminal repeat sequence (ITR). ATP7B has eight transmembrane domains that form a path through cell membranes for copper translocation; and a large N-terminus with six metal-binding domains (MBDs), each comprising approximately 70 amino acids and the highly conserved metal-binding motif GMxCxxC (where x is any amino acid). In addition to the canonical sequence (also called isoform a, which is the longest isoform; NCBI Reference Sequence: NP_000044.2), four additional isoforms are known: NCBI Reference Sequences four additional isoforms are known: NCBI Reference Sequences NP_001005918.1, NP_001230111.1, NP_001317507.1, NP_001317 508.1. The compositions and methods described herein may be used to treat subjects having a non-functional ATP7B variant protein which causes disease.

In one embodiment, a coding sequence for truncated human ATP7B (ATP7B Δ1-3-SS) (e.g., SEQ ID NO:1 or SEQ ID NO:15) encodes for a protein with amino acids as described in SEQ ID NO:8. SEQ ID NO:1 provides the cDNA for native human ATP7B that has MBDs 1-3 deleted. SEQ ID NO: 8 represents DEL1-3 Native or ATP7B Δ1-3-SS protein, in which two serine residues corresponding to positions 340 and 341 of the wild-type ATP7B full-length protein sequence are present.

In various embodiments described herein, vectors are provided that contain a genome comprising a coding sequence for truncated ATP7B (ATP7B Δ1-3-SS) (e.g., SEQ ID NO:1 or SEQ ID NO:15).

In some embodiments, vectors are provided that contain a genome comprising an engineered cDNA for human ATP7B, which has been codon-optimized (e.g., SEQ ID NO:15). The polypeptides delivered with the vectors described herein encompass truncated ATP7B in which MBDs 1-3 have been deleted (ATP7B Δ1-3-SS), which are suitable for use in treating WD.

In some embodiments, the polypeptide expressed with a vector described herein is a truncated human ATP7B (SEQ ID NO:8).

Vector Elements:

In some embodiments, the AAV vector contains a genome that further comprises one or more enhancer sequences. In one embodiment, the enhancer is selected from a transthyretin enhancer (enTTR), a cytomegalovirus immediate early gene (CMV) enhancer, a chicken β-actin (CBA) enhancer, an En34 enhancer, and an apolipoprotein (ApoE) enhancer. In an exemplary embodiment, the enhancer is the enTTR enhancer. In one embodiment, the enTTR enhancer comprises or consists of SEQ ID NO:3.

In some embodiments, the AAV vector contains a genome that further comprises one or more intron sequences. In one embodiment, the intron is selected from an SV40 Small T intron, a rabbit hemoglobin subunit beta (rHBB) intron, a human beta globin IVS2 intron, a β-globin/IgG chimeric intron (Promega chimeric intron), or an hFIX intron. In one exemplary embodiment, the intron is the SV40 Small T intron. In one embodiment, the SV40 Small T intron sequence comprises or consists of SEQ ID NO:4. In another exemplary embodiment, the intron is the rHBB intron. In one embodiment, the rHBB intron sequence comprises or consists of SEQ ID NO:5.

In some embodiments, the AAV vector contains a genome that further comprises a polyadenylation signal sequence. In one embodiment, the polyadenylation signal sequence is selected from an SV40 polyadenylation signal sequence, a bovine growth hormone (BGH) polyadenylation signal sequence, and a rabbit beta globin polyadenylation signal sequence. In an exemplary embodiment, the polyadenylation signal sequence is the bovine growth hormone (BGH) polyadenylation signal sequence. In one embodiment, the BGH polyadenylation signal sequence comprises or consists of SEQ ID NO:6. In another exemplary embodiment, the polyadenylation signal sequence is the SV40 polyadenylation signal sequence. In one embodiment, the SV40 polyadenylation signal sequence comprises or consists of SEQ ID NO:7.

AAV Capsids:

In another aspect, the application provides recombinant adeno-associated virus (rAAV) useful as agents for gene therapy in the treatment of WD, wherein said rAAV comprises an AAV capsid, and a vector genome as described herein. In some embodiments, the AAV capsid is from an AAV of serotype 9, 8, 1, 2, 3, 4, 5, 6, 7, 10, 11, 12, rh10, or hu37 (i.e., AAV1, AAV2, AAV3, AAV4, AAV5, AAV6, AAV7, AAV8, AAV9, AAV10, AAV11, AAV12, AAVrh10, or AAVhu37). In an exemplary embodiment, the AAV vector is an AAV serotype 9 (AAV9) vector, an AAV9 variant vector, an AAV serotype 8 (AAV8) vector, an AAV serotype 5 (AAV5) vector, or an AAV serotype 2 (AAV2) vector. In certain embodiments, the AAV capsid and vector are from an AAV9 serotype. In certain embodiments, the AAV capsid and vector are from an AAV8 serotype.

The AAV9 capsid is a self-assembled AAV capsid composed of multiple AAV9 VP proteins. The AAV9 VP proteins are typically expressed as alternative splice variants encoded by a nucleic acid sequence of SEQ ID NO:9 or a sequence that is at least 70%, at least 75%, at least 80%, at least 85%, at least 90%, at least 95%, at least 97%, at least 99% thereto, which encodes the capsid protein VP1 amino acid sequence of SEQ ID NO:10 (GenBank Accession: AAS99264). These splice variants result in proteins of different length of SEQ ID NO:10. In certain embodiments, an AAV9 capsid include an AAV9 capsid protein having an amino acid sequence which is 99% identical to AAS99264 or 99% identical to SEQ ID NO:10. See also U.S. Pat. No. 7,906,111, and international publication No. WO/2005/033321. As used herein, an AAV9 variant includes those described in, e.g., international publication No. WO/2016/049230, U.S. Pat. No. 8,927,514, U.S. Patent Publication No. 2015/0344911, and U.S. Pat. No. 8,734,809.

As indicated herein, the AAV9 capsid sequences and capsid proteins encoded by the sequences (e.g., nucleic acid sequence of SEQ ID NO:9 or amino acid sequence of SEQ ID NO:10 encoding AAV9 capsid protein VP1) are useful in the production of rAAV. However, in other embodiments, another AAV capsid is selected. Tissue specificity is determined by the capsid type. AAV serotypes which transduce a suitable target (e.g., liver, muscle, lung, or CNS) may be selected as sources for capsids of AAV viral vectors including, e.g., AAV1, AAV2, AAV3, AAV4, AAV5, AAV6, AAV6.2, AAV7, AAV8, AAV9, AAVrh10, AAVrh64R1, AAVrh64R2, AAVrh8. See, e.g., U.S. Patent Publication No. 2007/0036760; U.S. Patent Publication No. 2009/0197338; and EP1310571. See also international application No. WO 2003/042397 (AAV7 and other simian AAV), U.S. Pat. Nos. 7,282,199 and 7,790,449 (AAV8). In addition, AAV yet to be discovered, or a recombinant AAV based thereon, may be used as a source for the AAV capsid. These documents also describe other AAV which may be selected for generating AAV and are incorporated by reference. In some embodiments, an AAV capsid for use in the viral vector can be generated by mutagenesis (i.e., by insertions, deletions, or substitutions) of one of the aforementioned AAV capsids or its encoding nucleic acid.

Host Cells Comprising a Recombinant Nucleic Acid Molecule:

In some aspects, provided herein are host cells comprising a recombinant nucleic acid molecule, viral vector, e.g., an AAV vector, or a rAAV disclosed herein. In specific embodiments, the host cells may be suitable for the propagation of AAV.

A vast range of host cells can be used, such as bacteria, yeast, insect, mammalian cells, etc. In some embodiments, the host cell can be a cell (or a cell line) appropriate for production of recombinant AAV (rAAV), for example, a HeLa, Cos-7, HEK293, A549, BHK, Vero, RD, HT-1080, ARPE-19, or MRC-5 cell. In certain embodiments, the host cell line of the present invention is a HeLa cell line (e.g., HeLa S3). In another embodiment, host cell line of the present invention is a HEK293 cell line.

The recombinant nucleic acid molecules or vectors can be delivered into the host cell culture using any suitable method known in the art. In some embodiments, a stable host cell line that has the recombinant nucleic acid molecule or vector inserted into its genome is generated. In some embodiments, a stable host cell line is generated, which contains an AAV vector described herein. After transfection of the AAV vector to the host culture, integration of the rAAV into the host genome can be assayed by various methods, such as antibiotic selection, fluorescence-activated cell sorting, southern blot, PCR based detection, fluorescence in situ hybridization as described by Nakai et al., Nature Genetics (2003) 34:297-302; Philpott et al., Journal of Virology (2002) 76(11):5411-5421, and Howden et al., J. Gene Med. (2008) 10:42-50. Furthermore, a stable cell line can be established according to protocols well known in the art, such as those described in Clark, Kidney International Vol. 61 (2002):59-515, and Yuan et al., Human Gene Therapy (2011) 22(5):613-24.

Recombinant AAV for Gene Therapy:

Adeno-associated virus (AAV) belongs to the family Parvoviridae and the genus Dependovirus. AAV is a small, non-enveloped virus that packages a linear, single-stranded DNA genome. Both sense and antisense strands of AAV DNA are packaged into AAV capsids with equal frequency.

The AAV genome is characterized by two inverted terminal repeats (ITRs) that flank two open reading frames (ORF). The AAV2 genome, for example, the first 125 nucleotides of the ITR are a palindrome, which folds upon itself to maximize base pairing and forms a T-shaped hairpin structure. The other 20 bases of the ITR, called the D sequence, remain unpaired. The ITRs are cis-acting sequences important for AAV DNA replication; the ITR is the origin of replication and serves as a primer for second-strand synthesis by DNA polymerase. The double-stranded DNA formed during this synthesis, which is called replicating-form monomer, is used for a second round of self-priming replication and forms a replicating-form dimer. These double-stranded intermediates are processed via a strand displacement mechanism, resulting in single-stranded DNA used for packaging and double-stranded DNA used for transcription. Located within the ITR are the Rep binding elements and a terminal resolution site (TRS). These features are used by the viral regulatory protein Rep during AAV replication to process the double-stranded intermediates. In addition to their role in AAV replication, the ITR is also essential for AAV genome packaging, transcription, negative regulation under non-permissive conditions, and site-specific integration (Days and Berns, *Clin. Microbiol. Rev.* (2008) 21(4):583-593).

The left ORF of AAV contains the Rep gene, which encodes four proteins—Rep78, Rep68, Rep52 and Rep40. The right ORF contains the Cap gene, which produces three viral capsid proteins (VP1, VP2 and VP3). The AAV capsid contains 60 viral capsid proteins arranged into an icosahedral symmetry. VP1, VP2 and VP3 are present in a 1:1:10 molar ratio (Daya and Berns, *Clin. Microbiol. Rev.* (2008) 21(4):583-593).

AAV is currently one of the most frequently used viruses for gene therapy. Although AAV infects humans and some other primate species, it is not known to cause disease and elicits a very mild immune response. Gene therapy vectors that utilize AAV can infect both dividing and quiescent cells and persist in an extrachromosomal state without integrating into the genome of the host cell. Because of the advantageous features of AAV, the present disclosure contemplates the use of AAV for the recombinant nucleic acid molecules and methods disclosed herein.

AAV possesses several desirable features for a gene therapy vector, including the ability to bind and enter target cells, enter the nucleus, the ability to be expressed in the nucleus for a prolonged period of time, and low toxicity. However, the small size of the AAV genome limits the size of heterologous DNA that can be incorporated. To minimize this problem, AAV vectors have been constructed that do not encode Rep and the integration efficiency element (IEE). The ITRs are retained as they are cis signals required for packaging (Daya and Berns, *Clin. Microbial. Rev.* (2008) 21(4):583-593).

Methods for producing rAAV suitable for gene therapy are well known in the art (see, e.g., U.S. Patent Application Nos. 2012/0100606; 2012/0135515; 2011/0229971; and 2013/0072548; and Ghosh et al., *Gene Ther.* (2006) 13(4): 321-329), and can be utilized with the recombinant nucleic acid molecules and methods disclosed herein.

In some aspects, the application relates to the use of an rAAV disclosed herein for the treatment of Wilson disease (WD), wherein the rAAV includes an AAV capsid and a vector genome packaged therein. In some embodiments, the vector contains a genome comprising as operably linked components in 5' to 3' order: a 5'-inverted terminal repeat sequence (ITR), a promoter sequence, a coding sequence for a truncated human ATP7B (ATP7B Δ1-3-SS) (e.g., SEQ ID NO:1 or SEQ ID NO:15), and a 3'-inverted terminal repeat sequence (ITR). In an exemplary embodiment, the vector genome also comprises an enhancer sequence upstream of the promoter sequence, an intron downstream of the promoter, and a polyadenylation sequence upstream of the 3'-ITR. Thus, in another exemplary embodiment, the vector genome comprises as operably linked components in 5' to 3' order: a 5'-inverted terminal repeat sequence (ITR), an enhancer sequence, a promoter sequence, an intron sequence, a coding sequence for a truncated human ATP7B (ATP7B Δ1-3-SS) (e.g., SEQ ID NO:1 or SEQ ID NO:15), a polyadenylation signal sequence, and a 3'-inverted terminal repeat sequence (ITR). In a further exemplary embodiment, the vector genome comprises as operably linked components in 5' to 3' order: an AAV2 5'-ITR sequence, an enTTR enhancer, a TTR promoter, an SV40 Small T intron, a coding sequence for a truncated human ATP7B (ATP7B Δ1-3-SS) (e.g., SEQ ID NO:1 or SEQ ID NO:15), an SV40 polyadenylation signal sequence, and an AAV2 3'-ITR. In some embodiments, the vector genome further comprises a consensus Kozak sequence located downstream of the intron sequence. In some embodiments, the capsid is an AAV9 capsid.

In some aspects, the application relates to the use of a rAAV disclosed herein for the treatment of Wilson disease (WD), wherein the rAAV includes an AAV capsid and a vector genome packaged therein. In some embodiments, the vector genome comprises as operably linked components in 5' to 3' order: a 5'-inverted terminal repeat sequence (ITR), a promoter sequence, a coding sequence for a truncated human ATP7B (ATP7B Δ1-3-SS) (e.g., SEQ ID NO:1), and a 3'-inverted terminal repeat sequence (ITR). In an exemplary embodiment, the vector genome also comprises an enhancer sequence upstream of the promoter sequence, an intron downstream of the promoter, and a polyadenylation sequence upstream of the 3'-ITR. Thus, in another exemplary embodiment, the vector contains a genome comprising as operably linked components in 5' to 3' order: a 5'-inverted terminal repeat sequence (ITR), an enhancer sequence, a promoter sequence, an intron sequence, a coding sequence for a truncated human ATP7B (ATP7B Δ1-3-SS) (e.g., SEQ ID NO:1), a polyadenylation signal sequence, and a 3'-inverted terminal repeat sequence (ITR). In a further exemplary embodiment, the vector contains a genome comprising as operably linked components in 5' to 3' order: an AAV2 5'-ITR sequence, an enTTR enhancer, a TTR promoter, an SV40 Small T intron, a coding sequence for a truncated human ATP7B (ATP7B Δ1-3-SS) (e.g., SEQ ID NO:1), an SV40 polyadenylation signal sequence, and an AAV2 3'-ITR. In some embodiments, the packaged genome further comprises a consensus Kozak sequence located downstream of the intron sequence. In some embodiments, the capsid is an AAV9 capsid.

In some aspects, the application relates to the use of an rAAV disclosed herein for the treatment of Wilson disease (WD), wherein the rAAV includes an AAV capsid and a packaged vector genome. In some embodiments, the vector contains a packaged genome comprising as operably linked components in 5' to 3' order: a 5'-inverted terminal repeat sequence (ITR), a promoter sequence, a coding sequence for a truncated human ATP7B (ATP7B Δ1-3-SS) (e.g., SEQ ID NO:15), and a 3'-inverted terminal repeat sequence (ITR). In an exemplary embodiment, the packaged genome also comprises an enhancer sequence upstream of the promoter sequence, an intron downstream of the promoter, and a polyadenylation sequence upstream of the 3'-ITR. Thus, in another exemplary embodiment, the vector contains a packaged genome comprising as operably linked components in 5' to 3' order: a 5'-inverted terminal repeat sequence (ITR), an enhancer sequence, a promoter sequence, an intron sequence, a coding sequence for a truncated human ATP7B (ATP7B Δ1-3-SS) (e.g., SEQ ID NO:15), a polyadenylation signal sequence, and a 3'-inverted terminal repeat sequence (ITR). In a further exemplary embodiment, the vector contains a packaged genome comprising as operably linked components in 5' to 3' order: an AAV2 5'-ITR sequence, an enTTR enhancer, a TTR promoter, an SV40 Small T intron, a coding sequence for a truncated human ATP7B (ATP7B Δ1-3-SS) (e.g., SEQ ID NO:15), an SV40 polyadenylation signal sequence, and an AAV2 3'-ITR. In some embodiments, the packaged genome further comprises a consensus Kozak sequence located downstream of the intron sequence. In some embodiments, the capsid is an AAV9 capsid.

Figure 1:
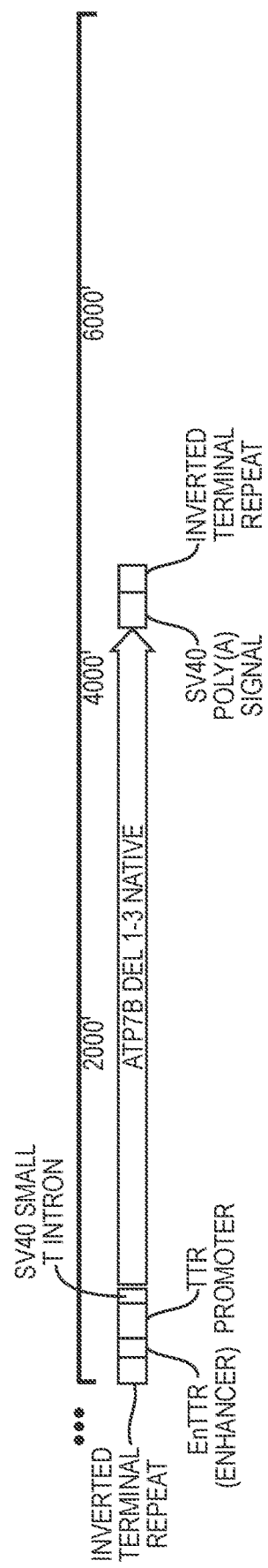
FIG. 1 is an illustrative diagram showing an exemplary vector genome construct comprising a nucleotide sequence, which encodes a truncated human copper-transporting ATPase 2 (ATP7B), in which the metal-binding domains (MBDs) 1-3 have been deleted, but the serine-rich loop including two serine residues (S340 and S341) between MBD3 and MBD4 is present ("ATP7B Δ1-3-SS" or "ATP7B dell-3 native"). Features of the exemplary vector genome construct are provided below.

An illustrative diagram showing an exemplary packaged vector genome construct for the expression of truncated ATP7B retaining MBDs 4, 5, and 6 is provided in FIG. 1. A 5'-ITR is represented by nucleotides 1-145; an enTTR enhancer is represented by nucleotides 146-245; a TTR promoter is represented by nucleotides 246-435; an SV40 Small T intron is represented by nucleotides 436-530; a consensus Kozak sequence is represented by nucleotides 531-536; a truncated ATP7B coding sequence is represented by nucleotides 540-4142; an SV40 polyadenylation signal sequence is represented by nucleotides 4143-4340; and a 3'-ITR is represented by nucleotides 4341-4485.

In certain embodiments, the nucleic acid sequence encoding ATP7B Δ1-3-SS is the native human sequence (represented by SEQ ID NO:1). Alternatively, in some embodiments, the nucleic acid sequence encoding ATP7B Δ1-3-SS is a codon-optimized human sequence (represented by SEQ ID NO:15).

Improved Efficacy in Treating WD:

In certain embodiments, the truncated human ATP7B (ATP7B Δ1-3-SS) encoded by SEQ ID NO:1 or SEQ ID NO:15, described herein, is more efficacious than the full-length or other truncated forms of ATP7B (e.g., ATP7B Δ1-4, SEQ ID NO:13). In some aspects, the ATP7B Δ1-3-SS of the present disclosure localizes to the Trans Golgi Network (TGN). In certain embodiments, a rAAV comprising the nucleic acid sequence of SEQ ID NO:1, which encodes ATP7B Δ1-3-SS, upon injection to a mammal diagnosed with a disorder of copper metabolism (e.g., Wilson disease), decreases the copper levels in the liver and urine of the mammal.

Improved Yield of AAV Vectors Comprising Truncated ATP7B:

In one aspect, the rAAV comprising the nucleic acid sequence encoding ATP7B Δ1-3-SS, packaged in AAV8 or AAV9, described herein, has about 1.1- about 10-fold higher (e.g., about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 3-fold, about 4-fold, about 5-fold, about 6-fold, about 7-fold, about 8-fold, about 9-fold, or about 10-fold) manufacturing yield than that of full-length ATP7B or the ATP7B Δ1-4.

Improved Yield of AAV Vector Comprising AAV9 Capsid:

In one aspect, the rAAV comprising the AAV9 capsid has about 1.1- about 10 fold higher (e.g., about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 3-fold, about 4-fold, about 5-fold, about 6-fold, about 7-fold, about 8-fold, about 9-fold, or about 10-fold) titer yield in comparison to rAAV comprising the AAV8 capsid.

Pharmaceutical Compositions:

Compositions comprising the rAAV disclosed herein and a pharmaceutically acceptable carrier are provided by the present disclosure. Suitable pharmaceutical formulations for administration of rAAV can be found, for example, in U.S. Patent Application Publication No. 2012/0219528. The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds, molecules or agents.

As highlighted in the preceding paragraph, the application relates in some aspects to pharmaceutical compositions comprising a rAAV of the invention. In some embodiments, the pharmaceutical composition comprises a pharmaceutically acceptable carrier or excipient. In some embodiments, the pharmaceutical composition is formulated for subcutaneous, intramuscular, intradermal, intraperitoneal, or intravenous administration. In an exemplary embodiment, the pharmaceutical composition is formulated for intravenous administration.

In some embodiments, the rAAV is formulated in a buffer/carrier suitable for infusion in human subjects. The buffer/carrier should include a component that prevents the rAAV from sticking to the infusion tubing but does not interfere with the rAAV binding activity in vivo. Various suitable solutions may include one or more of: a buffering saline, a surfactant, and a physiologically compatible salt or mixture of salts adjusted to an ionic strength equivalent to about 100 mM sodium chloride (NaCl) to about 250 mM NaCl, or a physiologically compatible salt adjusted to an equivalent ionic concentration. The pH may be in the range of 6.5 to 8.5, or 7 to 8.5, or 7.5 to 8. A suitable surfactant, or combination of surfactants, may be selected from among Poloxamers, i.e., nonionic triblock copolymers composed of a central hydrophobic chain of polyoxypropylene 10 (poly (propylene oxide)) flanked by two hydrophilic chains of polyoxyethylene (poly(ethylene oxide)), SOLUTOL HS 15 (Macrogol-15 Hydroxystearate), LABRASOL (Polyoxy capryllic glyceride), polyoxy 10 oleyl ether, TWEEN (polyoxyethylene sorbitan fatty acid esters), ethanol and polyethylene glycol.

Methods of Treating Wilson Disease:

In yet another aspect, the application relates to methods of treating WD in a human subject comprising administering to the human subject a therapeutically effective amount of a rAAV including SEQ ID NO:1 or SEQ ID NO:15 for encoding a truncated ATP7B (ATP7B Δ1-3-SS), disclosed herein.

In one embodiment, the application provides a method of treating WD comprising administering a rAAV that includes an AAV capsid and a packaged vector genome, wherein the vector genome comprises a coding sequence for a truncated human ATP7B (ATP7B 1-3-SS) (e.g., SEQ ID NO:1 or SEQ ID NO:15).

In yet another aspect, the application relates to methods of treating WD in a human subject comprising administering to a human subject diagnosed with at least one mutation in ATP7B, a therapeutically effective amount of at least one rAAV comprising a vector genome comprising a coding sequence for a truncated human ATP7B (ATP7B Δ1-3-SS) (e.g., SEQ ID NO:1 or SEQ ID NO:15). In one embodiment, the application provides a method of treating WD in a human subject diagnosed with at least one mutation in ATP7B comprising administering a rAAV that includes an AAV capsid and a packaged vector genome, wherein the vector genome comprises coding sequence for a truncated human ATP7B (ATP7B Δ1-3-SS) (e.g., SEQ ID NO:1 or SEQ ID NO:15). The coding sequence as represented by SEQ ID NO:1 encodes a truncated ATP7B represented by SEQ ID NO:8. In some embodiments, the capsid is an AAV9 capsid.

In yet another aspect, the application relates to methods of treating WD in a human subject comprising administering to a human subject diagnosed with at least one mutation in ATP7B, a therapeutically effective amount of at least one rAAV comprising a vector genome comprising a coding sequence for a truncated human ATP7B (ATP7B Δ1-3-SS)

(e.g., SEQ ID NO:1). In one embodiment, the application provides a method of treating WD in a human subject diagnosed with at least one mutation in ATP7B comprising administering a rAAV that includes an AAV capsid and a packaged vector genome, wherein the vector genome comprises coding sequence for a truncated human ATP7B (ATP7B Δ1-3-SS) (e.g., SEQ ID NO:1). The coding sequence as represented by SEQ ID NO:1 encodes a truncated ATP7B represented by SEQ ID NO:8. In some embodiments, the capsid is an AAV9 capsid.

In yet another aspect, the application relates to methods of treating WD in a human subject comprising administering to a human subject diagnosed with at least one mutation in ATP7B, a therapeutically effective amount of at least one rAAV comprising a vector genome comprising a coding sequence for a truncated human ATP7B (ATP7B Δ1-3-SS) (e.g., SEQ ID NO:15). In one embodiment, the application provides a method of treating WD in a human subject diagnosed with at least one mutation in ATP7B comprising administering a rAAV that includes an AAV capsid and a packaged vector genome, wherein the vector genome comprises coding sequence for a truncated human ATP7B (ATP7B Δ1-3-SS) (e.g., SEQ ID NO:15). In some embodiments, the capsid is an AAV9 capsid.

Any suitable method or route can be used to administer a rAAV or a rAAV-containing composition described herein. Routes of administration include, for example, systemic, oral, inhalation, intranasal, intratracheal, intraarterial, intraocular, intravenous, intramuscular, subcutaneous, intradermal, and other parenteral routes of administration. In some embodiments, the rAAV or a composition comprising a rAAV is administered intravenously.

The specific dose administered can be a uniform dose for each patient, for example, $1.0 \times 10^{11}$-$1.0 \times 10^{14}$ viral genome per kilogram of patient body weight (vg)/kg. Alternatively, a patient's dose can be tailored to the approximate body weight or surface area of the patient. Other factors in determining the appropriate dosage can include the disease or condition to be treated or prevented, the severity of the disease, the route of administration, and the age, sex and medical condition of the patient. Further refinement of the calculations necessary to determine the appropriate dosage for treatment is routinely made by those skilled in the art, especially in light of the dosage information and assays disclosed herein. The dosage can also be determined through the use of known assays for determining dosages used in conjunction with appropriate dose-response data. An individual patient's dosage can also be adjusted as the progress of the disease is monitored.

In some embodiments, the rAAV is administered at a dose of, e.g., about $1.0 \times 10^{11}$ vg/kg to about $1 \times 10^{14}$ vg/kg, about $5 \times 10^{11}$ vg/kg to about $5 \times 10^{13}$ vg/kg, or about $1 \times 10^{12}$ to about $1 \times 10^{13}$ vg/kg, as measured by qPCR or digital droplet PCR (ddPCR). In some embodiments, the rAAV is administered at a dose of about $2 \times 10^{12}$ vg/kg. In some embodiments, the rAAV is administered at a dose of about $5 \times 10^{12}$ vg/kg. In some embodiments, the rAAV is administered at a dose of about $6 \times 10^{12}$ vg/kg. In some embodiments, the rAAV is administered at a dose of about $1 \times 10^{13}$ vg/kg. In some embodiments, the rAAV is administered at a dose of about $7 \times 10^{13}$ vg/kg. The rAAV can be administered in a single dose, or in multiple doses (such as 2, 3, 4, 5, 6, 7, 8, 9, 10 or more doses) as needed for the desired therapeutic results. In some exemplary embodiments, only a single dose of a particular rAAV is administered.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present invention also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present invention remain operable. Moreover, two or more steps or actions may be conducted simultaneously.

The use of any and all examples, or exemplary language herein, for example, "such as" or "including" is intended merely to illustrate better the present invention and does not pose a limitation on the scope of the invention unless claimed. No language in the specification should be construed as indicating any non-claimed element as essential to the practice of the present invention.

EXAMPLES

The invention now being generally described, will be more readily understood by reference to the following examples, which are included merely for purposes of illustration of certain aspects and embodiments of the present invention, and is not intended to limit the invention.

Example 1—AAV Vectors and rAAV Produced from the Vectors

AAV Vector

This example describes construction of an AAV vector with the nucleic acid sequence represented by SEQ ID NO:1, bounded by two AAV2 inverted terminal repeats (ITRs, SEQ ID NO:2). SEQ ID NO:1 represents the cDNA for native human ATP7B that has MBDs 1-3 deleted. Nucleotides 223-225 in SEQ ID NO:1 encode for serine residue, S340 and nucleotides 226-228 in SEQ ID NO:1 encode for serine residue, S341 (numbering based on wild-type full length ATP7B protein sequence).

As illustrated in FIG. 1, within the AAV vector the ATP7B expression cassette contains an enhancer (EnTTR), a promoter (TTR), an intron (SV40 small T intron), the nucleotide sequence of SEQ ID NO:1, which encodes a truncated human ATP7B (ATP7B Δ1-3-SS), and an SV40 poly (A) signal. A circular map of the vector illustrating various components is shown in FIG. 2.

The AAV vector DTC319 contains a truncated human ATP7B sequence in which metal-binding domains 4, 5, and 6 are retained. The truncated human ATP7B sequence encodes for a protein that comprises two serine residues S340 and S341 (numbered according to NCBI Reference Sequence: NP_000044.2) represented by SEQ ID NO:8.

The Simian virus 40 (SV40) late polyadenylation signal (Genbank Accession No. J02400 (SEQ ID NO:7) provides a cis sequence for efficient polyadenylation of the ATP7B mRNA. This element functions as a signal for a specific cleavage event at the 3'-end of the nascent transcript and addition of a long polyadenyl tail.

Each truncated ATP7B expression cassette was cloned into an AAV vector. All AAV vectors had a backbone encoding the kanamycin-resistance gene. An exemplary AAV vector DTC319 is illustrated in FIG. 2. FIG. 1 depicts the expression cassette of DTC319, for expressing ATP7B (ATP7B Δ1-3-SS).

rAAV Virions

The AAV vector genome is a single-stranded DNA genome. Only the sequences between and inclusive of the ITR sequences are packaged into the AAV virion. Virions were produced by transfection of three plasmids into human embryonic kidney 293 (HEK293) cells, which provide E1a and E1b gene products. The first plasmid can be an AAV vector described herein. The second plasmid may be a packaging plasmid containing the wild-type AAV2 rep and AAV8 or AAV9 cap genes. The third plasmid is a helper adenovirus plasmid.

Illustration of an exemplary packaging plasmid, pAAV2/8.KanR (p2123FH) plasmid, is shown in FIG. 3. In this plasmid, the adeno-associated Rep/Cap plasmid pAAV2/8.KanR(p2123FH) (8354 bp) encodes the four wild-type AAV2 viral replication (Rep) proteins and the three wild-type AAV VP capsid (cap) proteins from serotype 8. Within the plasmid, the AAV p5 promoter that normally drives Rep gene expression has been moved from the 5'-end of the Rep region to the 3'-end of the AAV8 cap region. This arrangement introduces a spacer between the promoter and the Rep gene (i.e., the plasmid backbone) resulting in down-regulation of the expression of Rep and an increase in the ability to support high titer rAAV production. The gene for kanamycin resistance and the MB1 origin are included for plasmid production in E. coli.

Illustration of an exemplary helper plasmid, pAdDeltaF6 (Kan), is shown in FIG. 4. In this plasmid, regions of the adenovirus genome that are important for AAV replication, namely E2A, E4, and VA RNA, are provided. The adenovirus E1 functions are also required but are provided by the HEK293 host cells. The plasmid shown in FIG. 4 does not contain other adenovirus replication, structural genes, or the cis elements critical for adenovirus replication such as the adenoviral ITRs and therefore, no infectious adenovirus is expected to be generated. The gene for kanamycin resistance and the MB1 origin are included for plasmid production in E. coli.

Example 2—Deletion of Metal-Binding Domains (MBDs) 1-3 in Human ATP7B Improves Manufacturing Yield This example describes experiments, which demonstrated that ATP7B Δ1-3-SS had higher yield than the full-length ATP7B or the truncated form ATP7B Δ1-4.

Lack of functional ATP7B results in accumulation of copper in the liver and other tissues, which manifests as liver disease with neurological or psychiatric symptoms. WD can be treated by reducing copper absorption or removing excess copper from the body. C3He-Atp7b$^{tx-j}$ mice do not express functional Atp7b and thus serve as a mouse model for WD. AAV vectors containing the codon-optimized full-length human ATP7B sequence were used to transfect HEK293 cells with the Rep/Cap plasmid, which encodes four wild-type AAV2 viral replication (Rep) proteins and the three wild-type AAV VP capsid (cap) proteins, from serotype 8 and the helper plasmid to obtain ATP7BcoFL virus particles.

Male C3He-Atp7b$^{tx-j}$ mice were intravenously (i.v.) injected with either $10^{10}$ or $10^{11}$ GC/kg of ATP7BcoFL (full-length human ATP7B which has been codon-optimized). Female C3He-Atp7b$^{tx-j}$ mice were injected i.v. with either $10^9$, $10^{10}$, or $10^{11}$ GC/kg of the same vector. Liver copper levels in males (denoted by squares) and females (denoted by circles) were evaluated by inductively coupled plasma-mass spectrometry (ICP-MS), and compared to the copper levels from age-matched uninjected male and female heterozygous (Het) and C3He-Atp7b$^{tx-j}$ mice. Mice were necropsied at approximately 9 months of age and liver was harvested. Data is presented in FIG. 5.

Gene therapy utilizing AAV vectors can be used for treating WD. However, there is a limit to the size of the cDNA that can be packaged inside an AAV vector capsid. The wild type AAV genome is 4.7 kb, and packaging larger genomes can potentially reduce the yield and integrity of the DNA sequence encapsulated within the AAV capsid. Therefore, nucleotide sequence encoding ATP7B Δ1-3-SS was packaged within the AAV8 capsid, and manufacturing yield of ATP7B Δ1-3-SS was tested. AAV vectors encoding either full-length (FL) human ATP7B, human ATP7B in which MBDs 1-3 have been deleted, but the serine-rich loop including two serine residues (S340 and S341) between MBD3 and MBD4 is present (ATP7B Δ1-3-SS), or human ATP7B in which MBDs 1~4 have been deleted (ATP7B Δ1-4) were transfected into HEK293 cells. The Rep/Cap plasmid, which encodes four wild-type AAV2 viral replication (Rep) proteins and the three wild-type AAV VP capsid (cap) proteins from serotype 8, and the helper plasmid were co-transfected with the AAV vectors expressing various ATP7B proteins. FIG. 6 is a bar graph showing titers of rAAV produced from host cells after transfection of various AAV vectors. Y axis indicates total yield of each rAAV titer in genome copies (GC). The data show that ATP7B Δ1-3-SS had higher yield than the full-length or the ATP7B Δ1-4 truncated form.

Example 3—ATP7B Δ1-3-SS is More Efficacious in Restoration of Copper Metabolism in Comparison to ATP7B FL This example describes an experiment, which demonstrated that ATP7B Δ1-3-SS was more efficacious than ATP7B full-length (ATP7B FL) or ATP7B Δ1-4, in restoring copper metabolism in C3He-Atp7b$^{tx-j}$ mice.

As described above in Example 2, packaging a bulky cDNA sequence inside an AAV vector capsid can reduce the integrity of the DNA sequence and have potential quality issues. Therefore, truncated versions of human ATP7B were packaged within the AAV8 capsid and their efficacy in restoring copper metabolism was tested. $1.0 \times 10^{13}$ GC/kg of AAV8 vector encompassing either full length or truncated human ATP7B were administered to C3He-Atp7b$^{tx-j}$ mice. Liver and urine copper levels were evaluated by inductively coupled plasma-mass spectrometry. FIG. 7 is a scatter plot of urine and liver copper levels, squares and circles, respectively (μg/g), assayed after C3He-Atp7b$^{tx-j}$ mice were injected with AAV8 carrying full-length human ATP7B (ATP7B FL), ATP7B Δ1-3-SS, or ATP7B Δ1-4. FIG. 7 shows that ATP7B Δ1-3-SS is more efficacious than ATP7B full-length (ATP7B FL) or ATP7B Δ1-4, in restoring copper metabolism in C3He-Atp7b$^{tx-j}$ mice. Phosphate-buffered saline (PBS) administered C3He-Atp7b$^{tx-j}$ mice served as controls (vehicle).

Example 4—AAV Vector Comprising AAV9 Capsid Showed Higher Viral Production

This example describes an experiment which showed that production of an AAV vector comprising the AAV9 capsid generates a higher yield in comparison to the production of an AAV vector comprising the AAV8 capsid. Different AAV vectors were titrated by qPCR quantifying DNase-resistant particles (DRPs). FIG. 8 shows total yield of rAAV (titers in genome copies (GC)) produced from host cells after transfection of an AAV vector (DTC319) that encodes a truncated human ATP7B, in which the metal-binding domains (MBDs) 1-3 have been deleted, but the serine-rich loop including two serine residues (S340 and S341) between MBD3 and MBD4 is present, and co-transfected with a plasmid encoding either AAV8 capsid or AAV9 capsid.

Example 5—Therapeutic Properties of ATP7B Δ1-3-SS

This example describes animal studies, which demonstrated efficacy of ATP7B Δ1-3-SS (for example, DTC319, an rAAV vector that encodes a truncated human ATP7B, wherein metal-binding domains (MBDs) 1-3 have been deleted, but the serine-rich loop including two serine residues (S340 and S341) between MBD3 and MBD4 is present) in ameliorating symptoms of and treating Wilson disease (WD) in a mouse model (C3He-Atp7b$^{tx-j}$). In this example, three groups of male mice were evaluated: WD mice (C3He-Atp7b$^{tx-j}$ mice) administered either an AAV infusion of ATP7B Δ1-3-SS (for example, DTC319) encoded in an AAV8 vector or an intravenous injection of vehicle control (dilution buffer), and wild-type (WT) mice, which served as a negative control. For the infusion, rAAV was produced by triple transient transfection of adherent HEK cells and purified by Cesium Chloride gradient ultracentrifugation, a purification method well-known in the art. At the study endpoint, 4 weeks after infusion, mice from each group were evaluated for liver copper accumulation, ceruloplasmin activity, and liver pathology.

Liver copper accumulation was measured by inductively coupled plasma-mass spectrometry (ICP-MS), and demonstrated that liver copper level was significantly reduced in WD mice administered ATP7B Δ1-3-SS (for example, DTC319) (see FIG. 9, bar for DelA), compared to vehicle control. FIG. 9 shows liver copper accumulation levels (μg/g) in C3He-Atp7b$^{tx-j}$ mice after being administered an intravenous injection of a vehicle control (dilution buffer, bar for WD) or an infusion of AAV8 carrying native ATP7B Δ1-3-SS (bar for DelA). Liver copper accumulation levels in uninjected wild-type mice (WT) represented in the bar graph served as a negative control. Values expressed as mean±SEM.

Ceruloplasmin activity was significantly increased in WD mice after being administered ATP7B Δ1-3-SS (for example, DTC319) (see FIG. 10, bar for DelA). Ceruloplasmin activity was detected using an enzymatic reaction-based colorimetric activity assay as well-known in the art (See Schosinsky et. al., *Clin Chem.* 1974; 20(12):1556-63). FIG. 10 shows ceruloplasmin activity in C3He-Atp7b$^{tx-j}$ mice after receiving an intravenous injection of a vehicle control (dilution buffer, bar for WD) or an AAV infusion of ATP7B Δ1-3-SS encoded in an AAV8 vector (bar for DelA), as measured by an enzymatic reaction-based colorimetric activity assay. Ceruloplasmin activity in uninjected wild-type (WT) mice, as measured by the same enzymatic reaction-based colorimetric activity assay is also represented in the bar graph. The plot shows activity of ceruloplasmin as measured in optical density, OD as read at 540 nm. Values expressed as mean±SEM.

Liver was harvested from all animals in each group and stained with H&E (haematoxylin and eosin stain). H&E slides were assessed by a board certified pathologist for nuclear enlargement and hepatocellular hypertrophy, disorganization, inflammatory infiltrate, and hepatocellular necrosis according to the 0-4 scoring system. Scores from each mice in a group were averaged. FIG. 11 shows the average score as obtained after standard assessment of H&E slides for the animals in each group.

Example 6—AAV9 Gene Therapy as a Viable Therapy for Wilson Disease (WD)

This example describes use of rAAV particles comprising ATP7B Δ1-3-SS in treating WD in a subject. An AAV vector containing a nucleotide sequence encoding a truncated human ATP7B (ATP7B Δ1-3-SS), e.g., DTC319 (FIG. 2), a Rep/Cap plasmid, which encodes four wild-type AAV2 viral replication (Rep) proteins and the three wild-type AAV VP capsid (cap) proteins from serotype 9 (AAV9), and a helper plasmid, as described in Example 1, are co-transfected into a host cell. Harvested rAAV particles are then intravenously administered to a subject in need of WD therapy. Alternatively, a subject is administered rAAV particles that are harvested from host cell transfected with vector represented by FIG. 12, for treating WD.

INCORPORATION BY REFERENCE

The entire disclosure of each of the patent documents and scientific articles referred to herein is incorporated by reference for all purposes.

EQUIVALENTS

The disclosure may be embodied in other specific forms without departing from the spirit or essential characteristics thereof. The foregoing embodiments are therefore to be considered in all respects illustrative rather than limiting the disclosure described herein. Various structural elements of the different embodiments and various disclosed method steps may be utilized in various combinations and permutations, and all such variants are to be considered forms of the disclosure. Scope of the disclosure is thus indicated by the appended claims rather than by the foregoing description, and all changes that come within the meaning and range of equivalency of the claims are intended to be embraced therein.

---

What is claimed is:

1. A recombinant nucleic acid construct comprising:
   (a) a 5'-inverted terminal repeat (ITR) sequence;
   (b) a promoter sequence;
   (c) a nucleic acid sequence encoding the truncated human copper-transporting ATPase 2 (ATP7B) of SEQ ID NO: 8, in which metal-binding domains (MBDs) 1-3 have been deleted, but the serine-rich loop including two serine residues (S340 and S341) between MBD3 and MBD4 is present; and
   (d) a 3'-ITR sequence.

2. A recombinant adeno-associated virus (rAAV) useful for the treatment of Wilson disease, said rAAV comprising an AAV capsid and a vector genome packaged therein, said vector genome comprising:
   a. an AAV 5'-inverted terminal repeat (ITR) sequence;
   b. a promoter sequence;
   c. a nucleic acid sequence encoding the truncated human copper-transporting ATPase 2 (ATP7B) of SEQ ID NO: 8, in which metal-binding domains (MBDs) 1-3 have been deleted, but the serine-rich loop including two serine residues (S340 and S341) between MBD3 and MBD4 is present; and
   d. an AAV 3'-ITR sequence.

3. The rAAV of claim 2, wherein the AAV capsid is from an AAV of serotype 9, 8, 1, 2, 3, 4, 5, 6, 7, 10, 11, 12, rh10, or hu37.

4. The rAAV of claim 2, wherein the promoter sequence is selected from a transthyretin (TTR) promoter sequence, a chicken β-actin (CBA) promoter sequence, a cytomegalovirus (CMV) immediate early gene-(CMV) promoter sequence, a thyroxine binding globulin (TBG) promoter sequence, an alpha-1 anti-trypsin (A1AT) promoter sequence, and a CAG promoter sequence.

5. The rAAV of claim 2, wherein the AAV 5'-ITR sequence and/or the AAV 3'-ITR sequence is from AAV2.

6. The rAAV of claim 2, wherein the AAV 5'-ITR sequence and/or the AAV 3'-ITR sequence are from a non-AAV2 source.

7. The rAAV of claim 2, wherein the vector genome further comprises an enhancer sequence, and wherein said enhancer sequence is selected from a transthyretin enhancer (enTTR) sequence, a cytomegalovirus (CMV) immediate early gene enhancer sequence, a chicken β-actin (CBA) enhancer sequence, an En34 enhancer sequence, and an apolipoprotein (ApoE) enhancer sequence.

8. The rAAV of claim 7, wherein the enhancer sequence is located upstream of the promoter sequence.

9. The rAAV of claim 2, wherein the vector genome further comprises one or more intron sequences.

10. The rAAV of claim 9, wherein the one or more intron sequences is selected from an SV40 Small T intron sequence, a rabbit hemoglobin subunit beta (rHBB) intron sequence, a human beta globin IVS2 intron sequence, a β-globin/IG chimeric intron sequence, and an hFIX intron sequence.

11. The rAAV of claim 2, wherein the vector genome further comprises a polyadenylation signal sequence.

12. The rAAV of claim 11, wherein the polyadenylation signal sequence is selected from an SV40 polyadenylation signal sequence, a bovine growth hormone (BGH) polyadenylation signal sequence, and a rabbit beta globin polyadenylation signal sequence.

13. A recombinant adeno-associated virus (rAAV) comprising an AAV capsid and a vector genome packaged therein, said vector genome comprising:
   a. the AAV 5'-inverted terminal repeat (ITR) sequence of SEQ ID NO:2;
   b. the enhancer sequence of SEQ ID NO:3;
   c. the promoter sequence of SEQ ID NO: 12;
   d. the nucleic acid sequence of SEQ ID NO:1 or SEQ ID NO: 15 encoding a truncated human copper-transporting ATPase 2 (ATP7B); and
   e. the AAV 3'-ITR sequence of SEQ ID NO:2.

14. A composition comprising the rAAV of claim 13, and a pharmaceutically acceptable carrier.

15. A method of treating Wilson disease in a human subject comprising intravenously administering to the human subject a dose of about $1\times10^{11}$ genome copies (GC)/kg to about $1\times10^{14}$ genome copies of the rAAV of claim 2,
- wherein the AAV capsid is selected from: serotype 8 and serotype 9, and
- wherein the promoter sequence is selected from the group consisting of: a transthyretin TTR) promoter sequence, a chicken β-actin (CBA) promoter sequence, a cytomegalovirus (CMV) immediate early gene promoter sequence, a thyroxine binding globulin (TBG) promoter sequence, an alpha-1 anti-trypsin (A1AT) promoter sequence, and a CAG promoter sequence.

16. The method of claim 15, wherein the rAAV is administered at a dose of about $1\times10^{12}$ GC/kg to about $1\times10^{13}$ GC/kg.

17. The method of claim 15, wherein administering the rAAV comprises administration of a single dose of rAAV.

18. The method of claim 15, wherein administering the rAAV comprises administration of multiple doses of rAAV.

* * * * *

UNITED STATES PATENT AND TRADEMARK OFFICE
CERTIFICATE OF CORRECTION

| | | |
|---|---|---|
| PATENT NO. | : 12,338,450 B2 | Page 1 of 1 |
| APPLICATION NO. | : 17/417619 | |
| DATED | : June 24, 2025 | |
| INVENTOR(S) | : Christine Livingston and Samuel Wadsworth | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 958 days.

Signed and Sealed this
Sixteenth Day of December, 2025

John A. Squires
*Director of the United States Patent and Trademark Office*